(12) United States Patent
Fernandez-Pol

(10) Patent No.: US 6,410,570 B1
(45) Date of Patent: **\*Jun. 25, 2002**

(54) METHODS OF INACTIVATING A VIRUS AND CONTROLLING VIRAL REPLICATION

(75) Inventor: Jose A. Fernandez-Pol, Chesterfield, MO (US)

(73) Assignee: Novactyl, Inc., St. Louis, MO (US)

( * ) Notice: Subject to any disclaimer, the term of this patent is extended or adjusted under 35 U.S.C. 154(b) by 73 days.

This patent is subject to a terminal disclaimer.

(21) Appl. No.: 09/657,989

(22) Filed: Sep. 8, 2000

Related U.S. Application Data

(63) Continuation of application No. 09/127,620, filed on Aug. 1, 1998, now Pat. No. 6,127,393, which is a continuation-in-part of application No. 08/843,157, filed on Apr. 11, 1997, now abandoned, which is a continuation-in-part of application No. 08/581,351, filed on Dec. 29, 1995, now Pat. No. 5,767,135

(60) Provisional application No. 60/024,221, filed on Oct. 22, 1996, and provisional application No. 60/026,992, filed on Sep. 20, 1996.

(51) Int. Cl.$^7$ .............................. A61K 31/44; C12N 7/06
(52) U.S. Cl. ....................... 514/354; 435/238; 435/236; 514/13; 514/356; 514/934
(58) Field of Search ........................... 514/13, 354, 356, 514/934; 435/238, 236

(56) References Cited

U.S. PATENT DOCUMENTS

| | | |
|---|---|---|
| 3,903,285 A | 9/1975 | Umesawa et al. |
| 4,044,140 A | 8/1977 | Sherlock |
| 4,120,762 A | 10/1978 | Sviokla |
| 4,293,547 A | 10/1981 | Lewis et al. |
| 4,443,459 A | 4/1984 | Yano et al. |
| 4,814,351 A | 3/1989 | Mathews et al. |
| 5,057,320 A | 10/1991 | Evans et al. |
| 5,157,046 A | 10/1992 | Van Wauwe et al. |
| 5,164,414 A | 11/1992 | Vincent et al. |
| 5,173,486 A | 12/1992 | Monkovic et al. |
| 5,219,847 A | 6/1993 | Taguchi et al. |
| 5,284,840 A | 2/1994 | Rupprecht et al. |
| 5,391,537 A | 2/1995 | Takabe et al. |
| 5,403,816 A | 4/1995 | Takebe et al. |
| 5,484,951 A | 1/1996 | Kun et al. |
| 5,516,941 A | 5/1996 | Kun et al. |
| 5,536,743 A | 7/1996 | Borgman |
| 5,767,135 A | 6/1998 | Fernanedz-Pol |
| 6,001,555 A | 12/1999 | Henderson et al. |
| 6,127,393 A | * 10/2000 | Fernandez-Pol ............ 514/354 |

FOREIGN PATENT DOCUMENTS

| | | |
|---|---|---|
| WO | WO 9313789 | 7/1993 |
| WO | WO 9427627 | 12/1994 |

OTHER PUBLICATIONS

Patent Abstracts of Japan, vol. 14 No. 427, Jun. 25, 1990.
Database WPI, Section Ch, Week 9423, Derwent Publications Ltd., Apr. 19, 1994.
Antiproliferative Activity of Picolinic Acid Due to Macrophage Activation, Ruffman et al. 1987.
Mode of action of Zn–Complexes on Herpes Simplex Virus Type I Infection In Vitro, Varadinova et al, 1993.
Elisabetta Blasi, et al., Protective Effect of Picolinic Acid on Mice Intracerebrally Infected with Lethal Doses of *Candida albicans*; Antimicrobial Agents and Chemotherapy, Nov. 1993 pp. 2422–2426 vol. 37, No. 11.
Giovanni Melillo et al., Regulation of Nitric–oxide Synthase MRNA Expression by Interferon–y and Picolinic Acid, The Journal of Biological Chemistry vol. 269, No. 11, Issue of Mar. 18, pp. 8128–8133, 1994.
Elisabetta Blasi et al., Inhibition of Retroviral mRNA Expression In The Murine Macrophage Cell Line GG2EE by Biologic Response Modifiers, The Journal of Immumology vol. 141, pp. 2153–2157 No. 6 Sep. 15, 1988.
Takashi Mikogami et al., Effect of intracellular iron depletion by picolinic acid on expression of the lactoferrin receptor in the human colon carcinoma cell subclone HT29–18–C1, Biochem J. (1995) 308 391–397 (Printed in Great Britain).
George W. Cox et al., IL–4 Inhibits the Costimulatory Activity of IL–2 Or Picolinic Acid But Not Of Lipopolysaccharide on IFN–y–Treated Macrophages; The Journal of Immunology vol. 147 3809–3814 No. 11, Dec. 1, 1991.
Elisabetta Blasi et al., Pattern of cytokine gene expression in brains of mice protected by picolinic acid against lethal intracerebral infection with *Candida albicans*; Journal of Neuroimmunology 52 (1994) 205–213.
Giovanni Melillo, Picolinic Acid, a Catabolite of L–Tryptophan, Is a Costimulus for the Induction of Reactive Nitrogen Intermediate Production in Murine Macrophages; The Journal of Immunology vol. 140 4031–4040 No. 9 May 1, 1993.

(List continued on next page.)

*Primary Examiner*—Charanjit S. Aulakh
(74) *Attorney, Agent, or Firm*—Ahaji K. Amos; Thompson Coburn LLP; Caroline G. Chicoine

(57) ABSTRACT

An antiproliferative, antiinflammatory, antiinfective, immunization agent of a metal ion chelating agent such as picolinic acid or derivatives thereof, and methods of using the same. The agents chelate metals in metal containing protein complexes required for growth, replication or inflammatory response. The preparations can be administered systemically or for topical use. The preparations have antineoplastic, antiviral, antiinflammatory and antiproliferative effects and are used in the treatment of warts, psoriasis, acne, skin cancers, sunburn and other proliferative diseases and in the prevention of sexually transmitted diseases such as genital warts, herpes and AIDS. The agents also can be used to induce autologous immunological response.

25 Claims, 13 Drawing Sheets

OTHER PUBLICATIONS

Ann M. Bode et al., Inhibition of glucose–6–phosphate phosphohydrolase by 3–mercaptopicolinate and two analogs is metabolically directive; Biochem Cell Biol, vol. 71, 1993 pp. 113–121.

Vrooman et al., Picolinic Acid modulates kainic acid–evoked glutamate release from the striatum in vitro; Brain Research 627 (1993) 193–198.

Varesio et al., Ribosomal RNA Metabolism in Macrophages, Current Topics In Microbiology and Immunology vol. 181 1992.

Alan D. Frankel et al. Cellular Uptake of the Tat Protein from Human Immunodeficiency Virus, Cell, vol. 55, 1189–1193, Dec. 23, 1988.

J. Alberto Fernandez–Pol et al., Expression of Metallopanstimulin in Condylomata Acuminata of the Female Anogenital Region Induced by Papilloma Virus, Anticancer Research pp. 773–786 (1994).

Dennis J. Bobilya et al., Ligands Influence Zn Transport into Cultured Endothelial Cells, Society for Experimental Biology and Medicine pp. 159–166 (1993).

Stephan P. Clancy et al., Effects of Chromium Picolinate Supplementation on Body Composition, Strength, and Urinary Chromium Loss in Football Players; Original Research, International Journal of Sport Nutrition, 1994 142–153 1994 Human Kinetics Publishers, Inc.

Nancy A. Lee et al., Beneficial Effect of Chromium Supplementation on Serum Triglyceride Levels in NIDDM, Diabetes Care, vol. 17 No. 12 Dec. 1994.

T.G. Page et al. Effect of Chromium Picolinate on Growth and Serum and Carcass Traits of Growing–Finishing Pigs 1,2,3 J. Anim. Sci. 1993 71:656–662.

M.D. Lindemann Dietary Chromium Picolinate Additions Improve Grain: Feed and Carcass Characteristics in Growing–Finishing Pigs and Increase Litter Size in Reproducing Sows ; J. Anim. Sci. 1995 73: 457–465.

G. W. Evans et al., Chromium Picolinate Increases Membrane Fluidity and Rate of Insulin Internalization, Journal of Inorganic Biochemistry 46, pp. 243–250 (1992).

G. W. Evans et al. Composition and Biological Activity of Chromium–Pyridine Carboxylate Complexes, Journal of Inorganic Biochemistry 49, pp. 177–187 (1993).

J. A. Fernandez–Pol et al., Control of growth by picolinic acid: Differential response of normal and transformed cells; Cell Biology; vol. 74, No. 7 pp. 2889–2893, Jul. 1977.

J. A. Fernandez–Pol, Isolation and Characterization of a Siderophore–Like Growth Factor from Mutants of SV40–Transformed Cells Adapted to Picolinic Acid, Cell, vol. 14, 489–499, Jul. 1978.

J. Albert Fernandez–Pol, Growth Factors, Oncogencs, Antioncogenes and Aging, Geriatric Oncology, Chapter 7, pp. 60–75, 1992.

J. A. Fernandez–Pol, Morphological Changes Induced by Picolinic Acid in Cultured Mammalian Cells; Experimental and Molecular Pathology 29; 348–357 (1978).

J. A. Fernandez–Pol et al., NRK Cells Synchronized In GI By Picolinic Acid Are Super–Sensitive To Prostaglandin El Stimulation, vol. 74, No. 2; Febs Letters, Mar. 1977.

J. A. Fernandez–Pol, Peptide and Protein Complexes of Transition Metals as Modulators of Cellular Replication; International Journal of Nuclear Medicine and Biology, vol. 8 pp. 231–235 (1981).

J. A. Fernandez–Pol et al., Iron Transport In NRK Cells Synchronized In GI By Picolinic Acid, Cell Biology International Reports, vol. 2, No. 5, pp. 433–439 (1978).

J. A. Fernandez–Pol, Iron: Possible Cause of the GI Arrest Induced In NRK Cells By Picolinic Acid; Biochemical And Biophysical Research Communications, vol. 78, No. 1, pp. 136–143, 1977.

J. A. Fernandez–Pol, Transition Metal Ions Induce Cell Growth In NRKCells Synchronized In G1 By Picolinic Acid, vol. 76, No. 2, Biochemical And Biophysical Research Communications pp. 413–419 (1977).

Fernandez–Pol et al., Selective Toxicity Induced by Picolinic Acid in Simian Virus 40–transformed Cells in Tissue Culture, Cancer Research 37, 4276–4279, (Dec. 1977).

Michael L. Gargas et al., Urinary Excretion of Chromium by Humans Following Ingestion of Chromium Picolinate, Drug Metabolism and Disposition, vol. 22, No. 4 pp. 522–529 (1994).

Letter to the Editor; Chromium Picolinate is an Efficacious and Safe Supplement; International Journal of Sport Nutrition, 1993 p. II 7–122, 1993 Human Kinetics Publishers Inc.

R. J. Boegman et al., Neurotoxicity of Tryptophan Metabolities, Annals New York Academy of Sciences, vol. 585 1990 pp. 261–273.

Raymond I. Press, MD, et al., The Effect of Chromium Picolinate on Serum Cholesterol and Apoliprotein Fractions in Human Subject, West J Med 1990 Jan; 152:41–45.

Anna Shapiro et al. In Vivo and In Vitro activity by Diverse Chelators against *Trypanosoma brucei brucei,* The Journal of Protozoology, vol. 29, No. 1, Feb. 1982.

Komatsu, et al. Viral RNA Binding Properties of Human Immunodeficiency Virus Type–2 (HIV–2) Nucleocapsid Protein–Derived Synthetic Peptides, Biochemistry and Molecular Biology International, vol. 38, No. 6, May 1996.

William G. Rice et al., Science, vol. 270, Nov. 17, 1995, Inhibitors of HIV Nucleocapsid Protein Zinc Fingers as Candidates for the Treatment of AIDS.

Hathout et al., Characterization of Intermediates in the Oxidation of Zinc Fingers In Human Immunodeficiency Virus Type 1 Nucleocapsid Protein P7, Drug Metabolism and Disposition, vol. 24, No. 12.

Weizsacker et al., Gene Therapy for Chronic Viral Hepatitis: Ribozyrnes, Antisense Oligonucleotides, and Dominant Negative Mutants, Hepatology, Aug. 1997, pp. 251–255.

Theo Smart, Zinc Fingers: The Next Antiviral Target? GNMC Treatment Issues.

Priel et al., DNA binding properties of the zinc–bound and zinc–free IEV nucleocapsid protein: supercoiled DNA unwinding and DNA–protein cleavable complex formation.

Rein et al., Evidence that a Central Domain of Nucleocapsid Protein Is Required for RNA Packaging in Murine Leukemia Virus, Journal of Virology, vol. 68, No. 9 Sep. 1994, pp. 6124–6129.

Massami Otsuka et al., J. Med. Chem. 1994, 37, 4267–4269, Novel Zinc Chelators Which Inhibit the Binding of HIV–EPI (HIV Enhancer Binding Protein) to NF–KB Recognition Sequence.

Gorelick et al.; Genetic Analysis of the Zinc Finger in the Moloney Murine Leukemia Virus Nucleocapsid Domain: Replacement of Zinc–Coordinating Residues with Other Zinc–Coordinating Residues Yields Noninfectious Particles Containing Genomic RNA, Journal of Virology, Apr. 1996, pp. 2593–2597, vol. 70, No. 4.

William G. Rice et al., Nature, vol. 361, Feb. 4, 1993, Inhibition of HIV–1 infectivity by zinc–ejecting aromatic C–nitroso compounds.

Jon H. Condra et al., Science & Medicine, Jan. Feb. 1997, 14–23, Preventing HIV–1 Drug Resistance.

Peter J. Tummino, Proceedings of the National Academy of Sciences, vol. 93, No. 03, The in vitro ejection of zinc from human immunodeficiency virus (HIV) type 1 nulcleocapsid protein by disulfide benzamides with cellular anti–RIV activity.

Julian W. Bess, Jr. et al., Journal of Virology, Feb. 1992, pp. 840–847, vol. 66, No. 2, Tightly Bound Zinc in Human Immunodeficiency Virus Type 1, Human T–cell Leukemia Virus Type 1, and Other Retroviruses.

Jeremy M. Berg, The Journal of Biological Chemistry, vol. 265, No. 12, Issue of Apr. 25, pp. 6513–6516, Zinc Fingers and Other Metal–binding Domains.

Jeremy M. Berg, Science, vol. 232, Apr. 25, 1986, 486–487, Potential Metal–Binding Domains in Nucleic Acid Binding Proteins.

Thomas D. Mays, Department Of Health and Human Services, Federal Register, Aug. 10, 1995, vol. 60, No. 154.

Albert Fernandez–Pol Cytotoxic Activity of Fusaric Acid on Human Adenocarcinoma Cells in Tissue Culture; 1993 Anticancer Research 13; pp. 57–64.

R.J. Beninger et al., Neuroscience vol. 61, No. 3, pp. 603–612, 1994, Picolinic Acid Blocks The Neurotoxic But Not The Neuroexcitant Properties Of Quinolinic Acid In The Rat Brain: Evidence From Turning Behaviour And Tyrosine Hydroxylase Immunohistochemistry.

J. Cockhill et al. Action of Picolinic acid and Structurally related pyridinc carboxy on quinolinic acid–induced corticla cholingetic damage, 1992 Brain Research; 599, pp. 57–63 National Institutes of Health, Aug. 10, 1995, vol. 60, No. 154.

Skin–lightening preparations containing fusaric acids and/or picolinic acids. Chemical Abstracts, vol. 113, 1990, p. 359.

John J. Collins et al. Transient Growth Inhibition of *Escherichia coli* K–12 by Ion Chelators: "In Vivo" Inhibition of Ribonucleic Acid Synthesis; Journal of Bacteriology, Jun. 1979, pp. 923–932, vol. 138, No. 3.

Alan Rein et al. Inactivation of Murine Leukemia virus by Compounds That React with the Zinc Finger in the Viral Nucleocapsid Protein, Journal of Virology, Aug. 1996, pp. 4966–4972.

V. Wunderlich et al.; Medline; Disintegration of retroviruses by chelating agents; Archives of Virology, 1982 73 (2) 171–183.

B. Xu et al.; Medline; Efficacy of bimolane in the *Malessezia ovalis* model of psoriasis; Journal of Dermatology; 1991 Dec. 18 (12) 707–713.

Oxford et al.; Medline; Potential target sites for antiviral inhibitors of human immunodeficiency virus (HIV); Journal of Antimicrobial Chemotherapy (1989 Jan.) 23.

Edelman et al.; Medline; Treatment of bacterial vaginosis with intervaginal sponges containing metronidazole; Journal of Reproductive Medicine; (1989 May) 34 (5).

J. Albert Fernandez–Pol, Growth Factors, Oncogenes and Aging, Comprehensive Geriatric Oncology, pp. 179–196.

Gary W. Evans, An Inexpensive, Convenient Adjunct for the Treatment of Diabetes, The Western Journal of Medicine, Nov. 1991 p. 549.

X. Wang, A chelate theory for mechanism of action of aspirin–like drugs; Medical Hypotheses (1998) pp. 239–251.

Steven Brem; Angiogensis and Cancer Control: From Concept to Therapeutic Trial.

Turpin, et al.; Inhibitors of Human Immunodeficiency Virus Type 1 Zinc Fingers Prevent Normal Processing of Gag Precursors and Result in the Release of Noninfectious Virus Particles, Journal of Virology, Sep. 1996, pp. 6180–6189; vol. 70, No. 9.

\* cited by examiner

FIG. 4A
FIG. 4B
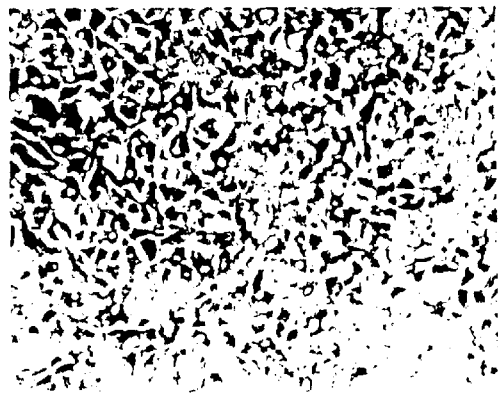
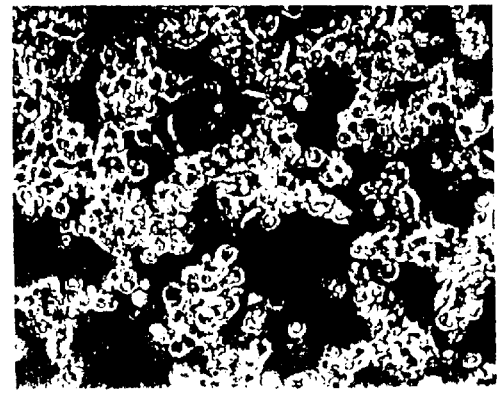
FIG. 4C
FIG. 4D

FIG. 5A
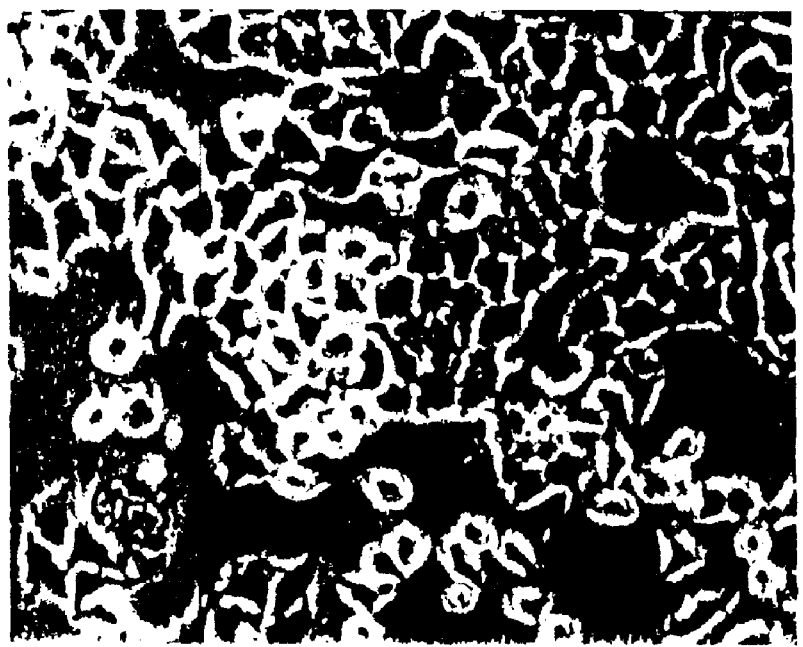
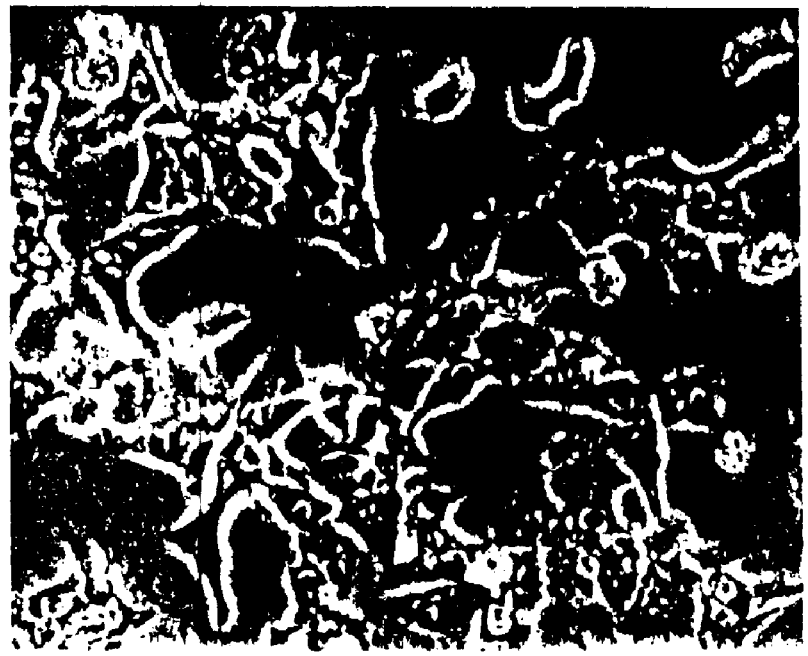
FIG. 5B

DISRUPTION OF ZINC FINGER BINDING DOMAINS
OF RETROVIRAL PROTEINS BY PA

NUCLEOCAPSID PROTEIN p7 gp 120 (SU)
gp41 (TM)
p55 (RT), p63
p11 (IN)
p6, 7, 9 (NC)
p24 (CA)
p17 (MA)

FIG. 9

METHODS OF INACTIVATING A VIRUS AND CONTROLLING VIRAL REPLICATION

CROSS-REFERENCE TO RELATED APPLICATIONS

This application is a continuation of application Ser. No. 09/127, 620, filed Aug. 1, 1998, now U.S. Pat. No. 6,127, 393, which is a continuation-in-part of application Ser. No. 08/843,157, filed Apr. 11, 1997, now abandoned, which is a continuation in part of application Ser. No. 08/581,351, filed Dec. 29,1995, now U.S. Pat. No. 5,767,135, and claims priority to provisional application Ser. No. 60/024,221, filed Oct. 22, 1996 and to provisional application Ser. No. 60/026, 992, filed Sep. 20, 1996.

STATEMENT REGARDING FEDERALLY SPONSORED RESEARCH OR DEVELOPMENT

None

BACKGROUND OF THE INVENTION

The invention relates to the treatment of and immunization against spontaneous and viral-induced infections, bacterial or parasitic infections, proliferative diseases and inflammatory diseases. More specifically the invention relates to the use of metal chelating materials including, picolinic acid, fusaric acid and their derivatives as chemotherapeutic and/or biological response modifier agents.

It will be appreciated that hereinafter the use of the term "response modifier" is intended to encompass all of the intended functions of the invention and method including antiviral, antiinfective, antiinflammatory, anticancer, vaccine and so on. Further, it will be appreciated that the broad term "antiinfective" is intended to include antibacterial, antifungal, antiparasitic functions, as well as actions against any other infective agent including viruses not encompassed by the term "antiviral".

Researchers recently have come to appreciate the role of metal containing proteins in proliferative and infectious diseases. Generally speaking, the inventor has studied the important function of proteins having amino acid sequences which bind metals, particularly transition metal ions therein. For example, the inventor has determined the important role zinc finger or zinc ring proteins in proliferative, inflammatory and infectious diseases.

The inventor and others have recognized at least three efficient approaches to inhibiting zinc finger proteins: 1) disruption of the zing finger by modification of the cysteins which are at least one of the four binding sites for $Zn^{2+}$ in the zinc finger protein which results in the ejection of zinc ion; 2) removal of the zinc from the zinc finger moiety by specific chelating agents; and 3) specific chelating agents that form a ternary complex at the site of zinc binding on zinc finger proteins, resulting in inhibition of the DNA or RNA binding activity of zinc finger proteins.

Papilloma virus infection results in a number of proliferative diseases in subjects including warts induced by type 4 human papilloma virus (common warts). Moreover, papilloma virus can cause plantar ulcers as well as plantar warts. Human papilloma virus infection of the uterine cervix is the most common of all sexually transmitted diseases. Commonly know as genital warts, this wide spread virus infection is a serious disease that potentially can develop into cervical cancer. Since the virus is permanently present in cells, infection recurs in a significant percentage of patients. In many instances, conization of the uterine cervix is required to remove the infected tissue.

Condylomata acuminata, also denoted genital warts, are benign epithelial growths that occur in the genital and perianal areas and caused by a number of human papilloma viruses (HPV) including types 6,11 and 54. These are low risk viruses which rarely progress to malignancy. However, high risk viruses such as HPV-16 and HPV-18 are associated with cervical intraepithelial cancer.

The actions of HPV are mediated by specific viral-encoded proteins which interact and/or modulate cellular DNA and proteins to produce abnormal growth and differentiation of cells. Two proteins of the HPV viral genome, E6 and E7, are well conserved among anogenital HPV's and both may contribute to the uncontrolled proliferation of basal cells characteristics of the lesions. The E7 oncoprotein is a multi-functional protein with transcriptional modulatory and cellular transforming properties. The E7 oncoprotein is denoted as a "zinc finger" protein because it pocesses a sequence motif that is implicated in zinc binding. A strong correlation between zinc binding and the transactivation activity of E7 has been documented. The HPV-16 E6 protein is a "zinc finger" protein that binds DNA and may have transcriptional properties such that its function may be dependent upon the formation of zinc fingers. E6 protein can complex with the cellular tumor suppressor protein p53 and it is necessary with E7 protein for the immortalization of primary human squamous cells. Only two proteins of HPV are consistently expressed and integrated in keratinocytes, the E6 and E7 zinc finger proteins. The E6 and E7 proteins are responsible for continuous cell proliferation. About twenty HPVs are associated with ano-genital lesions and all transformed keratinocytes of these lesions contain E6 and E7 zinc finger proteins. The E6 and E7 regulate growth and transformation by interfering with cellular p53 and pRb proteins, respectively. Thus, one should be able to control or cure HPV by inactivating E6 and E7, the critical zinc finger proteins which are required for replication. When replication of the virus is halted, apoptosis of the virally-infected cells must occur. Thus, one can alter the epidemiology of, for example, carcinoma of the uterine cervix by interfering with the function of zinc finger or zinc ring proteins.

The human immunodeficiency virus (HIV) encodes several regulatory proteins that are not found in other retroviruses. The tat protein, which is one of these proteins, trans-activates genes that are expressed from the HIV long terminal repeat and tat is essential for viral replication. The tat protein of the HIV-1 is a zinc finger protein that when added to certain cells in tissue culture, specifically promotes growth. It has been shown that the tat protein of HIV-1 stimulates growth of cells derived from Kaposi's sarcoma lesions of AIDS patients. Other experiments raised the possibility that tat might act as a viral growth factor to stimulate replication in latently infected cells or alter expression of cellular genes.

The nucleocapsid p7 protein of HIV has been targeted by the inventor for treatment of HIV viral infections. The p7 protein is required for the correct assembly of newly formed virus particles during the viral life cycle. Moreover, the p7 protein contains two zinc fingers that are required for the recognition and packaging of the viral RNA. Because the zinc finger domain is essential for nucleic acid binding, p7 resistant mutants are highly unlikely to occur. Thus, agents that effectively attack the two zinc finger domains of the HIV virus nucleocapsid p7 in vivo will decrease the overall number of viral particles that bud off and exit the cells to infect other cells.

Further, the hepatitis C viruses are dependent upon the Zn 2+ metalloproteinases for specific viral functions.

It is of interest to note that the breast cancer susceptibility gene BRCA 1 includes a zinc ring domain that are involved in protein-protein interactions or protein-DNA interactions. It also is of interest to note that the zinc ring domain of the BRCA 1 has a 54% sequence similarity and 38% sequence identity with a zinc ring domain encoded by the genome of the equine herpes virus. (R. Bienstock, "Molecular Modeling of Proteins Structures, *Science & Medicine*, January/Febuary 1997, p.56).

From the foregoing it appears that it would be beneficial to have a product that can interfere with the formation or action of certain zinc finger proteins or zinc ring proteins to stop the progress of certain virally induced or mediated proliferative diseases or to halt the progress of viruses or malignancies dependent upon zinc finger or zinc ring proteins for their transformation and immortalization. Furthermore, it would be beneficial to provide a product that can halt the growth of other proliferative cells, such as malignant cells by chelating metal ions from zinc-dependent or transition metal ion (e.g. copper, iron, etc.) dependent proteins and enzymes necessary for the replication of the malignant cells.

BRIEF SUMMARY OF THE INVENTION

It is among the objects of the present invention to provide a compound which can retard the growth and proliferation of target viruses or cells by blocking the activity of metal ion-containing proteins.

Another object of the present invention to provide a compound which can retard the growth and proliferation of target infective organisms including bacteria, fungi, parasites or other infective agents by blocking the activity of metal ion-containing proteins.

Another object of the present invention is to provide a compound which can retard the growth and proliferation of target viruses or cells by blocking the activity of transition metal ion-containing protein structures such as zinc finger or zinc ring proteins associated with replication.

It is another objects of the present invention to provide a compound that can retard the growth of premalignant and malignant cells such as virally, chemically and spontaneously transformed cells.

It is also among the objects of the present invention to provide a new treatment for patients suffering from various forms of spontaneous and retroviral-induced proliferative diseases and cancers by utilizing the novel properties of metal chelating agents as a chemotherapeutic/anti-viral agent and/or biological response modifier.

It is another object of the present invention to provide an agent that can halt the proliferation and transmission of the HIV virus.

It is another object of the invention to provide a method of halting the function of zinc finger proteins, zinc ring proteins, and other proteins with zinc binding motifs heretofore unidentified by the administration of a zinc chelating agent, both topically and systemically.

Another object of the invention to provide a method of halting the function of metal containing protein structures containing metals other than zinc, metal-containing ring proteins structures, and other proteins with metal binding motifs heretofore unidentified by the administration of a metal chelating agent, both topically and systemically.

Another object of the invention is to provide an antiinflammatory compound that is effective in a broad range of inflammatory disorders including symptoms of well-know autoimmune diseases as well as inflammatory response to infections and to chemical assault or radiation including, but not limited to, ultraviolet, atomic or medical radiation.

Yet another object of the invention is to provide such chelating agents in a relatively safe and nontoxic form such as picolinic acid or its derivatives for both topical and systemic use.

Another object of the invention is to provide a topical preparation of metal chelating agents such as picolinic acid or its derivatives to treat virally induced or spontaneous proliferative diseases of the skin or mucous membranes in human and animal subjects.

It is still another object of the present invention to provide an intravaginal preparation containing metal chelating agents such as picolinic acid or derivatives thereof that can prevent or retard sexually transmitted diseases caused by viruses or other causative agents containing zinc finger proteins or zinc ring proteins.

Still another object of the present invention is to provide a preparation containing chelating agents such as picolinic acid or derivatives thereof that halts the progression of viral infections or proliferative diseases that is non-toxic to normal cells, easy to use, relatively inexpensive and well suited for its intended purposes.

According to the invention, briefly stated, a method or treatment and compound used in the method, for example, metal chelating compounds, such as picolinic acid or derivative thereof, for the treatment of infective or proliferative diseases, actinic lesions, inflammatory response, radiation assault, and cancers in human and animal subjects, as well as the method of treatment. The invention can be used orally or topically to treat or control a wide assortment of proliferative diseases or conditions, both spontaneous or induced by viruses, bacteria, fungi, chemicals, ultraviolet light for example. The metal chelating compounds bind metal, for example iron or transition metal ions such as zinc, required by enzymes, heat shock proteins or by transcription proteins found in viruses or malignant cells. By way of further example, the metal chelating compound, for example picolinic acid or its derivatives, is used to bind the zinc-containing p7 protein common to the HIV virus, thereby inactivating the virus and preventing the exit of RNA containing viruses or particles from the cells.

One embodiment of a topical preparation consists of a solution of the chelator, for example, 0.01% to 99%, preferably 5% to 25%, picolinic acid in deionized water and is applied to the lesion one or two times a day. The preparation can be applied to toe nails and finger nails, for example, to treat fungal infections. In another embodiment, the topical preparation consists of an ointment or cream containing approximately 0.5% to 99%, preferably 5% to 20% picolinic acid which is applied once or twice daily to the lesion and to a bandage placed on the lesion. The ointment or cream can be instilled intravaginally to retard sexually transmitted viral diseases.

The various embodiments of the topical preparation can be used to treat papilloma and herpes viral diseases and to retard the papilloma, herpes and HIV 1 viruses as well as proliferative diseases such as psoriasis, actinic lesions and skin cancer.

Various active derivatives that maintain their activity and stability when after systemic administration are provided. Slow release oral formulations can be used to treat diseases for the digestive tract. The active derivatives can be administered orally, parenterally, by inhalation, transdermally or by any other appropriate method to control proliferative diseases, cancers, viral infections, HIV, and any other condition wherein the causative agent includes a zinc-containing protein, whether the zinc-containing protein is a zinc finger protein, a zinc ring protein, or other type of zinc or metal containing structure heretofore unidentified or undetected, wherein the metal containing segment is required for protein stability and configuration.

It will be appreciated that other appropriate chelating materials such as the derivative of picolinic acid, fusaric acid, also may be used. It also will be appreciated that, although 5% to 20% topical preparations of the picolinic acid are described, a broader range of concentrations may be used. For example from approximately 0.001% to 99.9% metal chelating agent may be used. Further, the systemic doses may be altered or adjusted to ranges greater or lesser than those described, depending on toxicity and patient response, without departing from the scope of the appended claims.

BRIEF DESCRIPTION OF THE SEVERAL VIEWS OF THE DRAWINGS

In the drawings.

FIG. 4A illustrates the effects of fusaric acid on morphology of WI-38 cells, the cells treated without fusaric acid;

FIG. 4B illustrates the effects of fusaric acid on morphology of WI-38 cells, the cells treated with fusaric acid;

FIG. 4C illustrates the effects of fusaric acid on morphology of LoVo cells, the cells treated without fusaric acid;

FIG. 4D illustrates the effects of fusaric acid on morphology of LoVo cells, the cells treated with fusaric acid;

FIG. 5A illustrates the effects of fusaric acid on morphology of KB cells, the cells treated without fusaric acid;

FIG. 5B illustrates the effects of fusaric acid on morphology of KB cells, the cells treated with fusaric acid;

FIG. 9 illustrates disruption of zinc finger binding domains in retroviral proteins caused by picolinic acid;

DETAILED DESCRIPTION OF THE INVENTION

Figure 1:
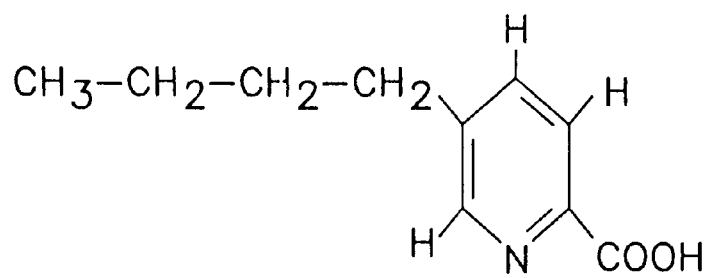
FIG. 1 is the chemical structure of fusaric acid.

Picolinic acid, a metal chelating, naturally occurring, biological compound, inhibits the growth of numerous cultured normal and transformed mammalian cells. It has been shown that short-term treatment with picolinic acid arrests normal cells in $G_1$, (Go) while transformed cells are blocked in different phases of the cell cycle. With longer exposure to picolinic acid cytotoxicity and cell death was observed in all transformed cells whether they were blocked in $G_1$, $G_2$ or at random. In contrast, most normal cells showed no toxic effects from the picolinic acid. Thus, the selective growth arrest and the differential cytotoxicity induced by picolinic acid reveals a basic difference in growth control and survival mechanism(s) between normal and transformed cells.

Kinetic and radiosotopic studies show that picolinic acid both inhibits incorporation of iron into the cells and effectively removes radioiron from the cells. Hence, it is conceivable that the inhibition of cell proliferation in vitro, as well as tumor growth in vivo, by picolinic acid results, at least in part, from selective depletion of iron in the cells.

However, it also is shown that picolinic acid may arrest prokaryote and eukaryote cell growth by inhibiting Zn-requiring enzymes. In addition to its chelating ability, picolinic acid has a number of biologic properties such inhibitory effects on ADP ribosylation and ribosomal RNA maturation, modulation of hormonal responses, and macrophage activation. Picolinic acid in combination with interferon gamma can inhibit retroviral J2 mRNA expression and growth in murine macrophages. Thus, picolinic acid and its derivatives can act as a biological response modifier.

The inventor has determined that picolinic acid and fusaric acid were found to inhibit the zinc dependent binding of recombinant MPS-1 to DNA, as determined by gel shift assays and the data correlates with the absence of radioactive Zn65 from recombinant MPS-1 protein. MPS-1 is a ubiquitous tumor marker and cell growth stimulator and is described in detail in the inventor's U.S. Pat. No. 5,243,041. MPS-1 has one zinc finger domain of the type CCCC. Picolinic acid and fusaric acid react with the CCCC zinc finger to remove radioactive Zn65 from MPS-1. This is detected by a change in the electrophoretic mobility of MPS-1 under non-denaturing conditions. These experiments indicate that picolinic acid and derivatives should remove zinc and denature various types of zinc finger or zinc ring proteins, whether known or heretofore undiscovered, including viral proteins such as nucleocapsid p7 proteins, as will be explained further. Furthermore, the inventor has determined that any chemical compound, whether known or heretofore undiscovered, that will remove the zinc (or other metal) and denature the proteins or that will form a ternary complex (protein-zinc-chelator) can be effective as a therapeutic agent or as an autologous immune response modulator, as will be discussed in greater detail below.

Fusaric acid is a potent inhibitor of cancerous cell growth. Fusaric acid, a picolinic acid derivative, metal ion chelator, shows an effect on the growth and viability of normal and cancerous cells in tissue culture. Examples presented here show that fusaric acid has potent anti-cancer and anti-viral activity in vitro. Moreover, fusaric acid may be useful in the treatment of spontaneous and virally-induced tumors in vivo without substantially damaging living normal cells.

Fusaric acid is the 5-butyl derivative of picolinic acid. Its structure is shown in FIG. 1. Fusaric acid was recognized in the early 1960's to have activity as an antihypertensive agent in vivo. Fusaric acid and its properties can be summarized as follows. Undoubtedly the drug interacts with various metalloproteins and metal ion-requiring enzyme systems. Fusaric acid is noted to be an inhibitor of a wide variety of seemingly unrelated enzyme systems. These include poly ADP ribose polymerase, a Zn-finger enzyme, and other Zn-finger proteins. Cu-requiring systems are also effected by fusaric acid. These enzymatic systems are important in growth control mechanisms. It has become increasingly clear that fusaric acid, by virtue of its butyl group penetrates the cell interior much more easily than picolinic acid, and works at least in part as a Zn/Cu chelating agent.

As mentioned above, the hepatitis C family of viruses are dependent upon metalloproteinases having a zinc finger domain for replication of the virus.

Novel substituted derivatives of picolinic acid and related compounds can be used systemically to treat cancer, viral infections and other related diseases and proliferative disorders. The novel substituted derivatives of picolinic acid and related compounds also work by disrupting the binding of zinc atoms in zinc finger proteins, zinc ring proteins or other structures heretofore unknown that depend upon the inclusion of zinc or other metal ions such as transition metal ions, for stability, packaging or replication. Further, the novel substituted derivatives are stable and retain their zinc chelating properties even when introduced systemically by injection, oral administration, inhalation or transdermal or other routes of administration.

Figure 11:
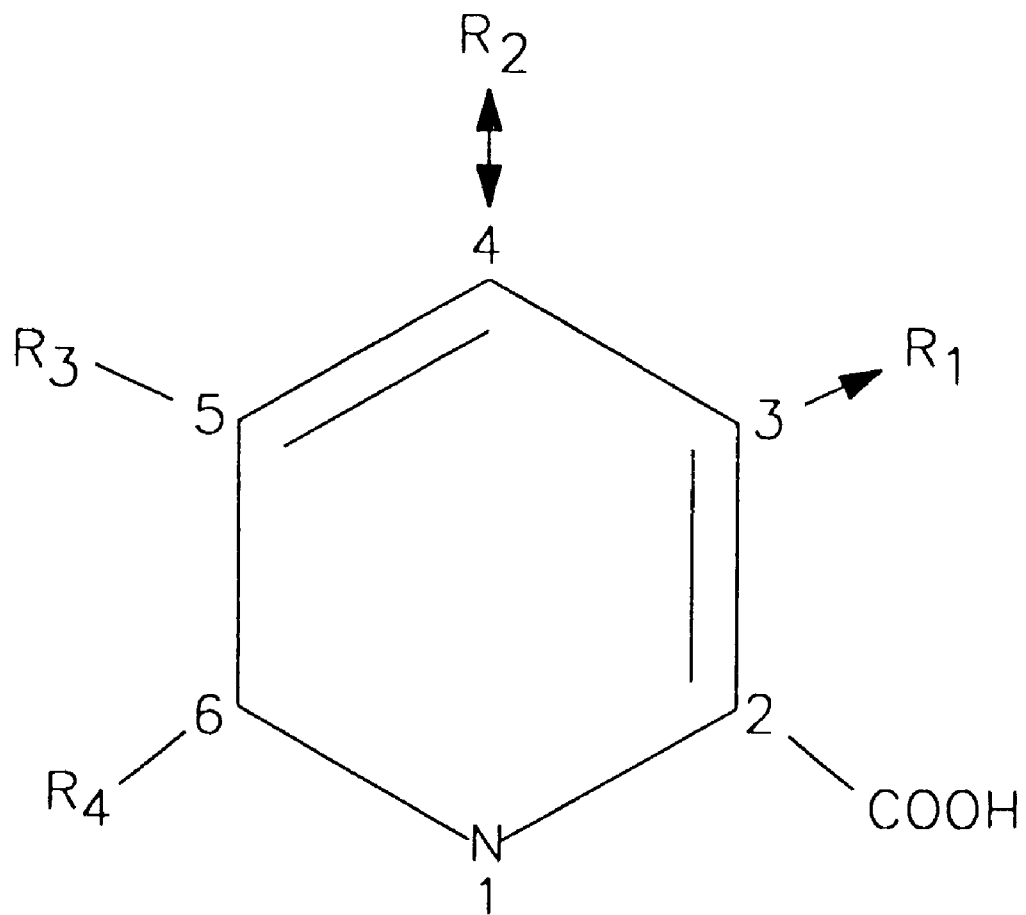
FIG. 11 illustrates the molecular structure of a derivatives of picolinic acid for system use.

FIG. 11 illustrates novel derivatives of picolinic acid for systemic use. Computer modeling indicates that such derivatives can interact with zinc atoms and disrupt its binding to the zinc finger protein. Substitutions at positions 3, 4,5 and 6 on the 2-pyridine carboxylic acid (picolinic acid) have the proper configuration to prevent interference with the zinc finger protein backbone. For example R1, R2, R3 or R4 can be a methyl, ethyl, propyl, isopropyl, butyl, isobutyl, secondary butyl, tertiary butyl, pentyl, isopentyl, neopentyl or similar group. Further, substitution with halogens such as fluorine, chlorine, bromine and iodine can result in effective, systemically active agents. The systemic compounds can be prepared by methods generally known to the art and include pharmacologically acceptable salts thereof.

Figure 12:
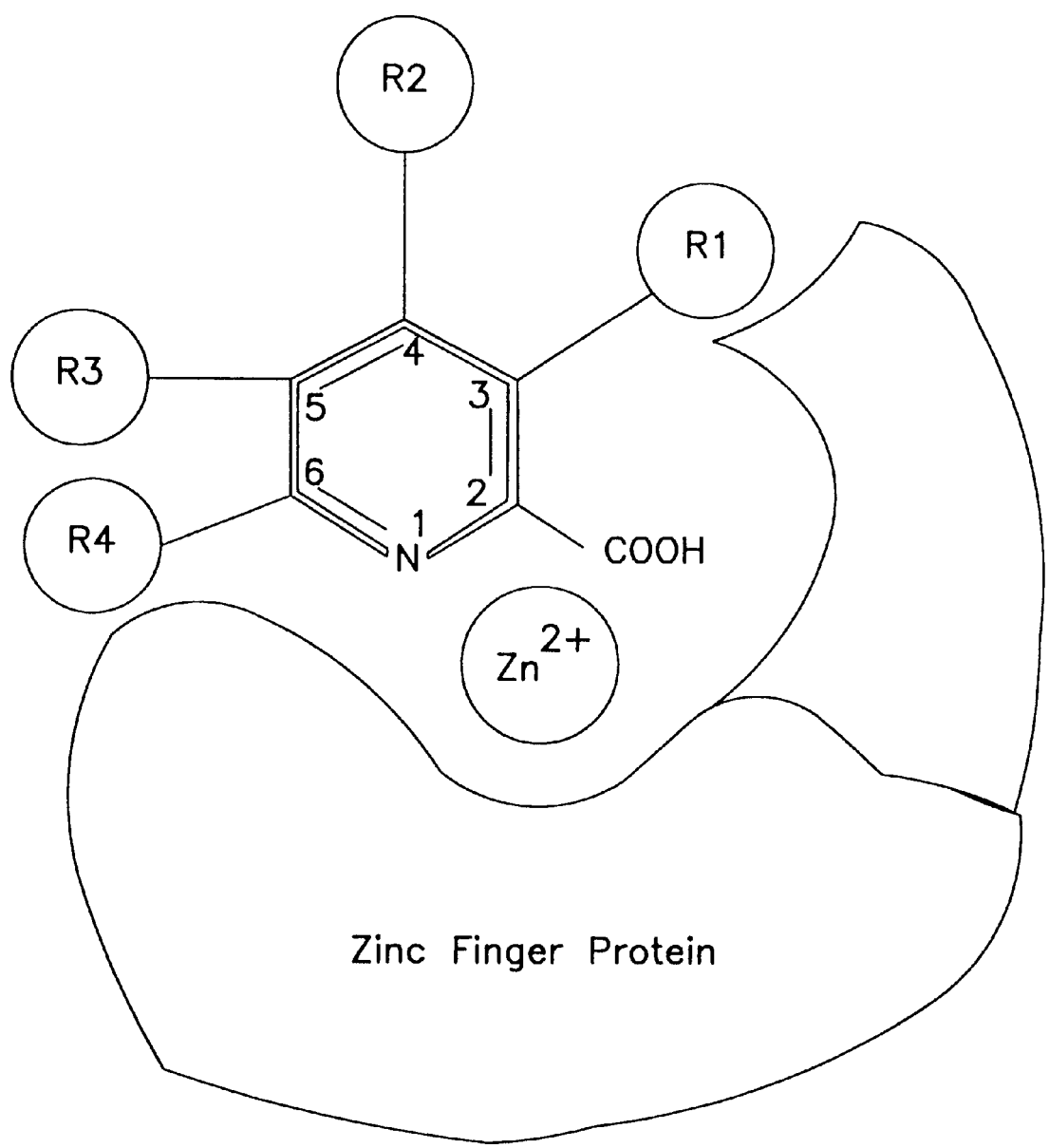
FIG. 12 illustrates the binding of a picolinic acid derivative to zinc and adjacent amino acids of a zinc finger protein.
Figure 13:
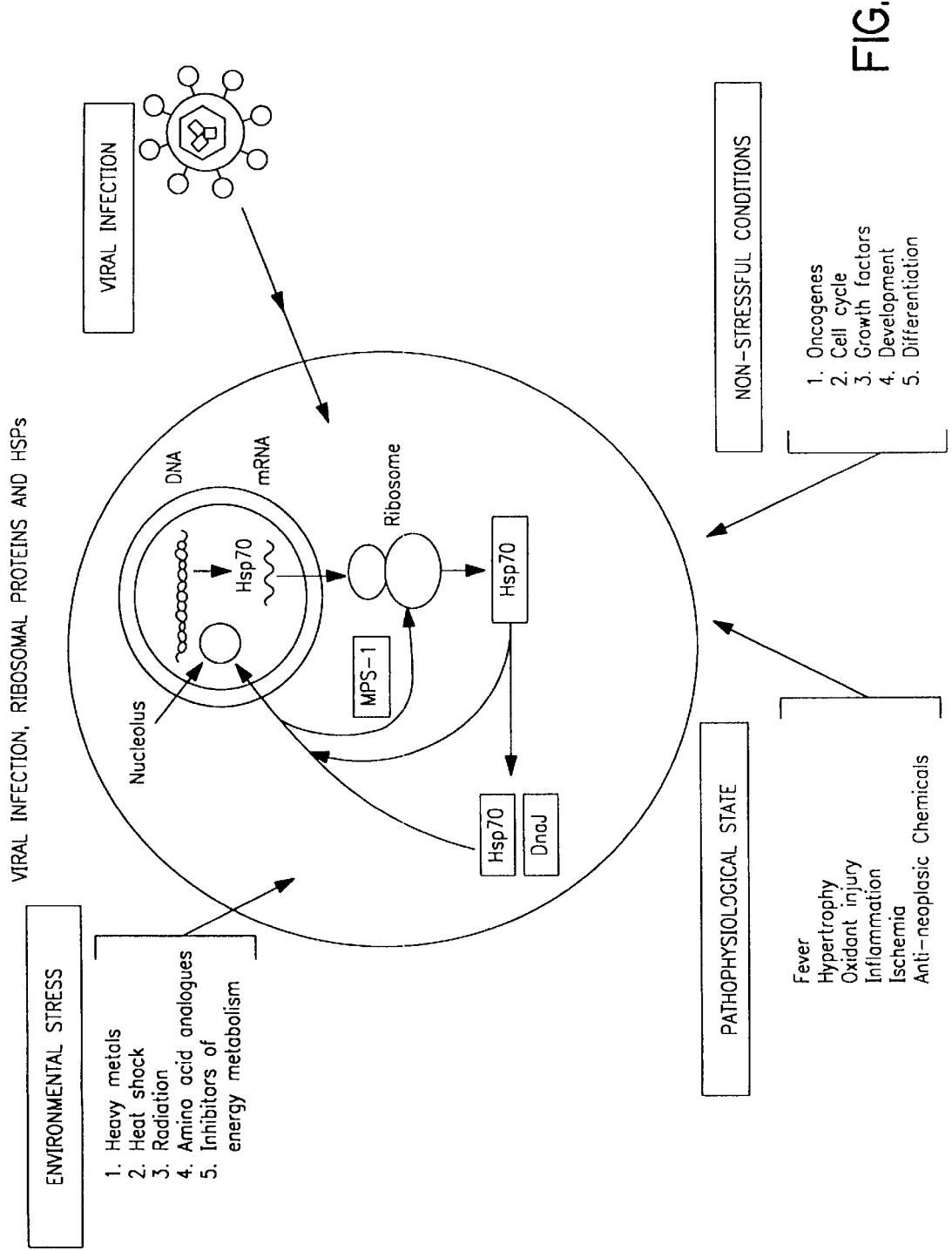
FIG. 13 is a schematic illustrating the interrelation of viral infection, ribosomal proteins and the zinc finger heat shock protein, DnaJ which is involved in inflammation.

FIG. 12 illustrates the binding of zinc in a zinc finger or zinc ring protein by derivatives of picolinic acid. Further, as shown in FIG. 12, the substituted positions at positions 3, 5 or 6 i.e. R1, R3 or R4 can attach to amino acids on each side of the zinc thus binding the zinc containing protein at three sites and forming ternary complex comprised of the protein, the zinc, and the picolinic acid derivative which inactivates the protein. Therefore, the above-listed moieties that can be substituted at the various positions can result in a picolinic acid derivative that not only is more stable for systemic administration, but also one that has even greater affinity and specificity for, and binding potential with, various zinc finger or zinc ring proteins.

It will be appreciated that substitutions at the 3,4,5 and 6 positions can be may be made with a peptide of sixteen amino acids or more with either basic or acid amino acids predominating. The substituted picolinic acid would have an increased molecular weight and a substantially increased half-life in the blood. Further, such compounds would penetrate the virus-containing cells more effectively due to the amphipathic nature of the peptide residues.

The systemic compounds can be administered to human and animal subjects by any means that produces contact of the active agent with the target protein, such as orally, parenterally, inhalation, transdermally, rectally, on any other method for obtaining a pharmacologically acceptable blood level. In general, a pharmacologically effective daily does can be from about 0.01 mg/kg to about 25 mg/kg per day or any other pharmacologically acceptable dosing. It will be appreciated that picolinic acid derivatives referred to herein as the systemic compounds can be employed in the hereinafter described topical preparations as well as employed systemically. Furthermore, the claimed invention is intended to include any other chemical compounds, either derivatives of picolinic acid, compounds with structural relationships to picolinic acid, or heretofore unknown compounds that function to chelate, attach to, or modify metal ions in proteins structures, including, but not limited to transition metal ions found in proteins structures of viruses, proliferative cells (plant or animal) or even as components of fungi and bacteria.

Figure 6:
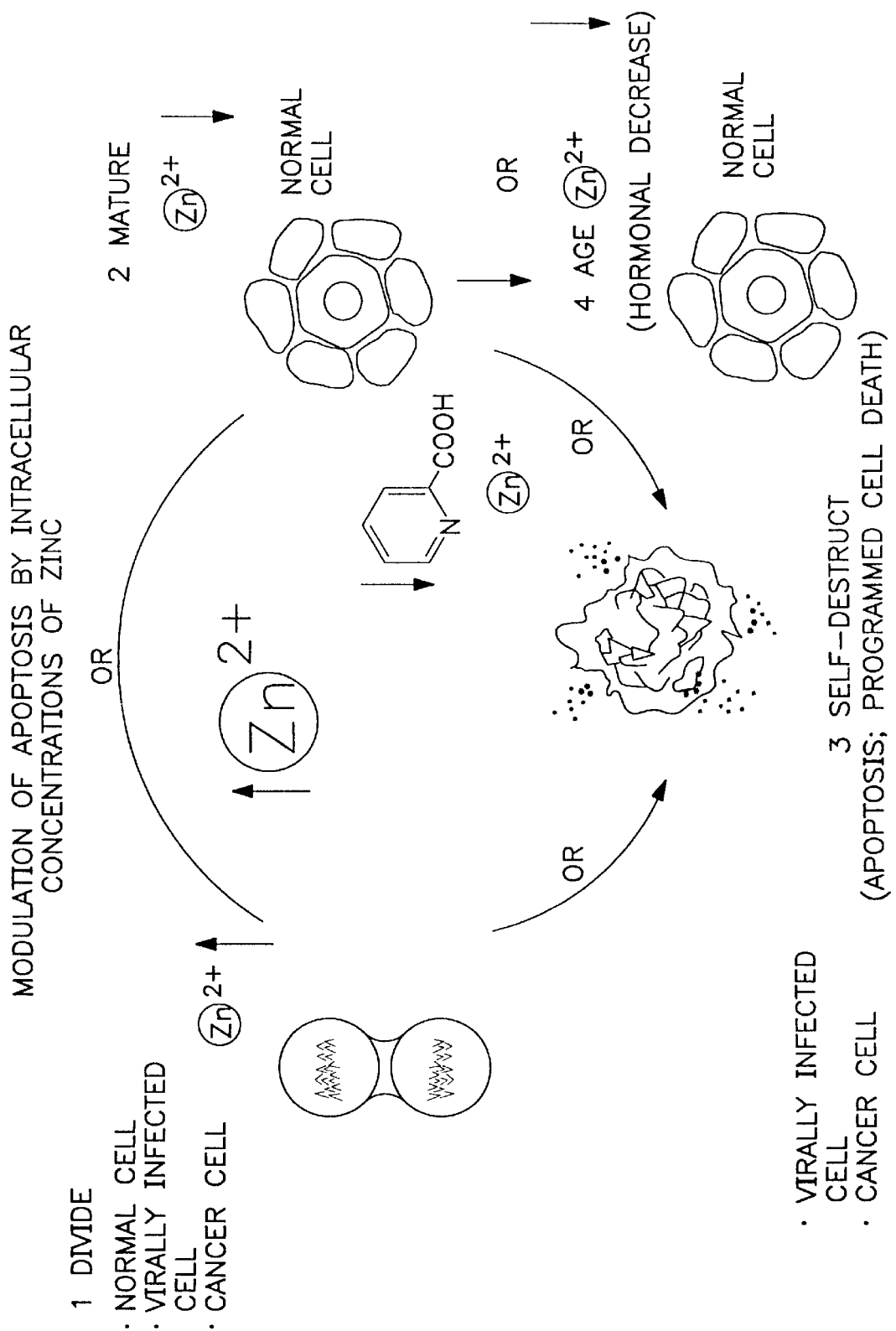
FIG. 6 illustrates modulation of apoptosis by intracellular concentrations of zinc.
Figure 7:
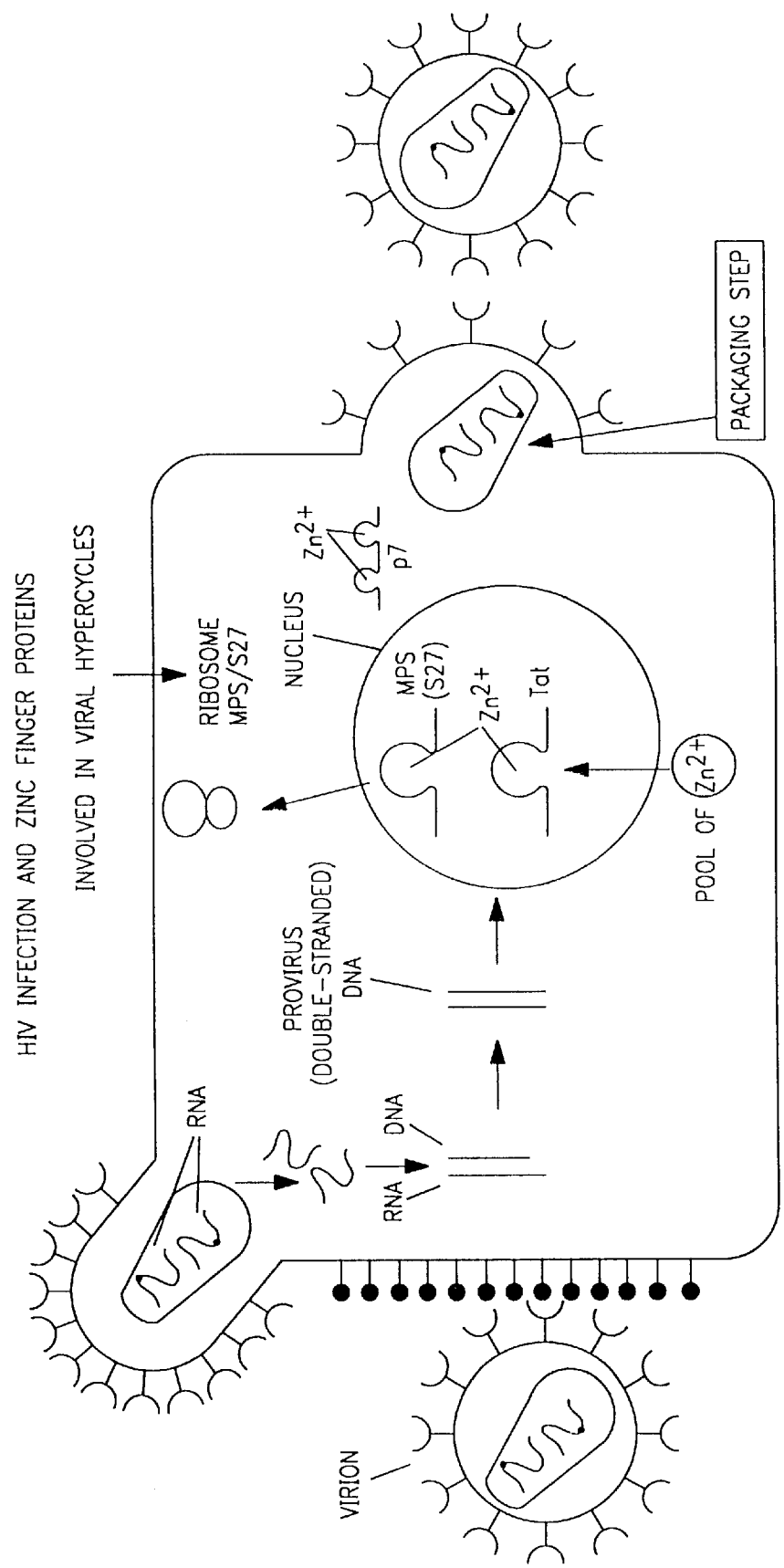
FIG. 7 illustrates the role of zinc finger proteins in HIV infection.
Figure 8:
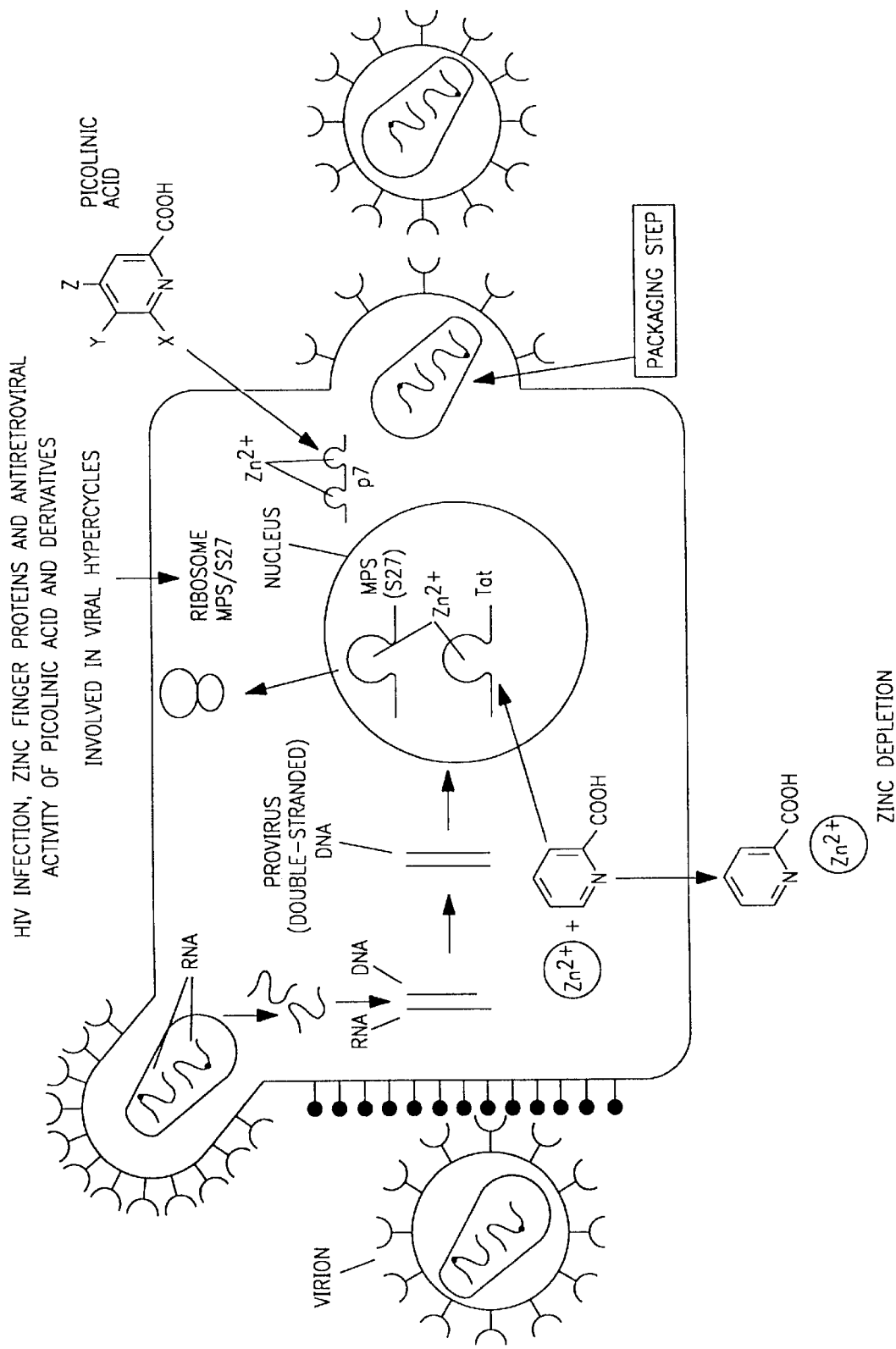
FIG. 8 illustrates the effect of picolinic acid and derivatives on HIV, zinc finger proteins and retroviruses.
Figure 10:
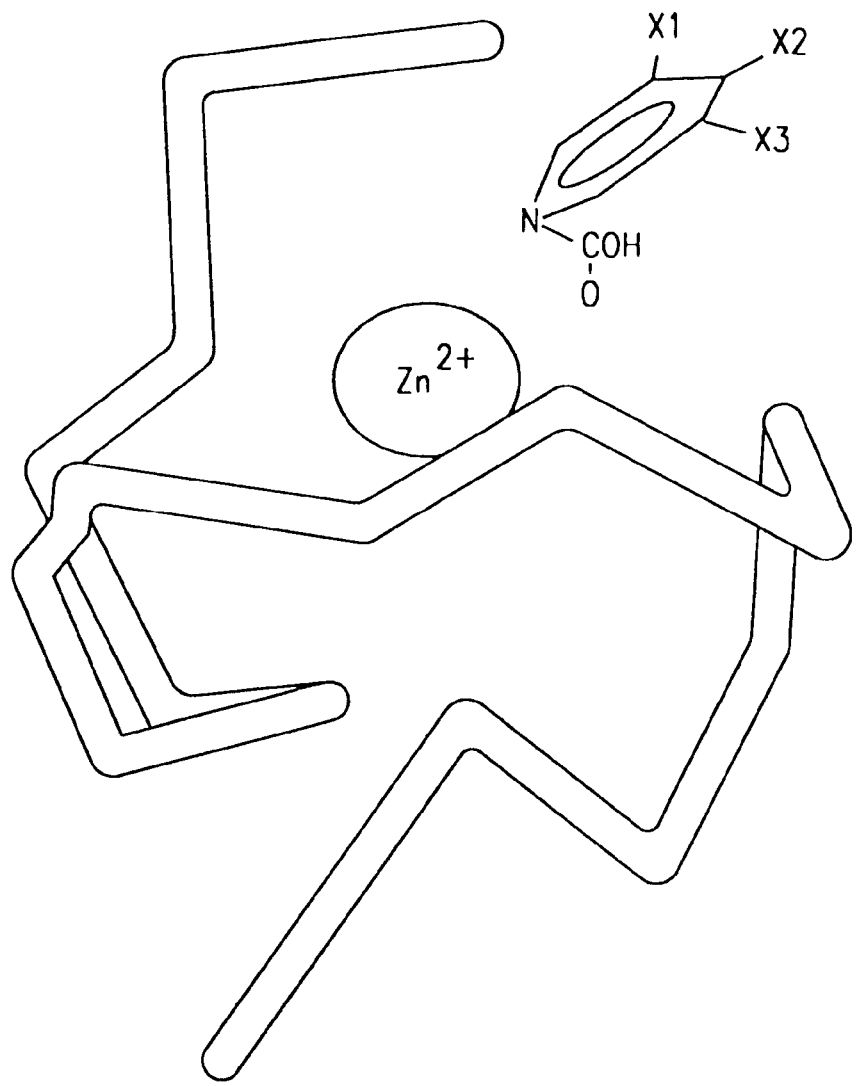
FIG. 10 illustrates the wide spectrum of antiviral activity of picolinic acid.

It previously has been discovered that p7 protein is required for correct assembly of newly formed virus particles during the viral life cycle, as explained above. By modeling, the inventor has discovered the activity of picolinic acid in disrupting zinc finger proteins in retroviruses, as is illustrated in FIGS. 6–10. FIG. 6 illustrates modulation of apoptosis by intracellular concentrations of zinc; FIG. 7 illustrates the role of zinc finger proteins in HIV infection; FIG. 8 illustrates the effect of picolinic acid and derivatives on HIV, zinc finger proteins and retroviruses; FIG. 9 illustrates disruption of zinc finger binding domains in retroviral proteins caused by picolinic acid; and FIG. 10 illustrates the wide spectrum of antiviral activity of picolinic acid.

The p7 protein contains two zinc fingers that are required for the recognition and packaging of viral RNA. In one embodiment and aspect of the invention, the inventor has targeted p7 for drug therapy with picolinic acid and derivatives. Picolinic acid and derivatives are zinc finger disrupting agents that act by attacking the two zinc finger domains of the virus (i.e. HIV) nucleocapsid p7 in vitro. This results in picolinic acid and derivatives inducing an overall decrease in the number of viral particles that bud off and exit the cells to infect other cells. It is known that HIV-1 contains two zinc fingers in the retroviral p7 protein. The zinc fingers are highly conserved throughout essentially all retroviruses. Thus, mutations in the zinc fingers of the HIV-1 virus will produce a non-infectious HIV-1 particle. Because the zinc finger domain is essential for nucleic acid binding, p7 resistant mutants will not occur. The picolinic acid can be used, therefore, for prevention of retroviral and other viral diseases by, for example, inhibiting exit of the virus or virus particles from the cells or by chemically inducing a non-infectious virus. Furthermore, any chemical entity, either known or unknown at this time, that functions in the same manner as picolinic acid or its derivatives, is intended to be encompassed by the instant invention. Representative viruses which include zinc finger or zinc ring proteins are included on Table 1.

TABLE 1

Examples Of Families Of Viruses Using Zinc Finger Proteins, Zinc Ring Proteins Or Transition Metal Ion-Dependent Enzymes For Replication And/Or Virulence

| Virus protein and Mr | Location and general Characteristics | Protein Function and Specific Properties |
|---|---|---|
| Reovirus | | |
| Lambda-1, 140 Kd | Inner capsid | Zinc finger protein Binds dsDNA |
| Rho-3, 41 Kd | Outer capsid | Zinc finger protein Binds dsRNA |
| Rotavirus | | |

TABLE 1-continued

Examples Of Families Of Viruses Using Zinc Finger Proteins, Zinc Ring Proteins Or Transition Metal Ion-Dependent Enzymes For Replication And/Or Virulence

| Virus protein and Mr | Location and general Characteristics | Protein Function and Specific Properties |
|---|---|---|
| NSP1, 53 Kd | Non-structural | Zinc finger protein RNA binding |
| Retroviridae | | |
| Ncp7 (AIDS) 55 amino acids | Nucleocapsid | Zinc finger protein RNA binding Required for inclusion of RNA in virions |
| TAT (AIDS) 82–101 amino acids | Regulatory protein Trans-activator | Cluster of 7 cystein residues |
| Papillomavirus | | |
| E6 | Regulatory protein | Zinc finger protein Transforming protein of HPVs Continuous cell proliferation Targets degradation of p53 |
| E7 | Regulatory protein | Zinc finger protein Transforming protein of HPVs Continuous cell proliferation Binds to the retinoblastoma protein, Rb |
| Adenovirus | | |
| E1A | Regulatory protein | Zinc finger protein Gene expression Transforming protein |
| Hepatitis C | | |
| NS2(+NS3) | Zn-dependent enzyme | Zn-metalloproteinase |
| Herpes viruses | | |
| HSV-1: ICPO protein | Regulatory protein | Zinc finger DNA-binding Trans-activation |
| HSV-2: MDBP protein | Regulatory protein | Zinc finger protein ssDNA-binding DNA replication |
| ICP6: Ribonucleotide Reductase | Fe-dependent Enzyme | Synthesis of DNA precursors |
| Equine Herpes virus-1 ZR protein | Regulatory protein | Zinc ring configuration DNA binding Protein/protein interactions |

Examples of the specific effects of metal chelating agents, including picolinic acid, substituted picolinic acid derivatives and fusaric acid, as well as the practical application of those agents will now be described:

EXAMPLE 1

Effects of Picolinic Acid on Growth of WI-38, LoVo and KB, Cells

Cells were plated at $1.5 \times 10^5$ cells/60-mm dish; 48 hours later, the medium was removed, and new media with or without 3 mM picolinic acid were added. Total cell protein was determined at the indicated times; each point is the average of triplicate measurements from 2 cultures.

The growth of normal WI-38 cells was inhibited by 3 mM picolinic acid within 24 hours, the cells showed no toxic effects for up to 72 hours of treatment, and the inhibition was reversible within 24 hours of removal of the agent (data not shown). These results are identical to previous results with WI-38 cells incubated with picolinic acid.

Figure 2:
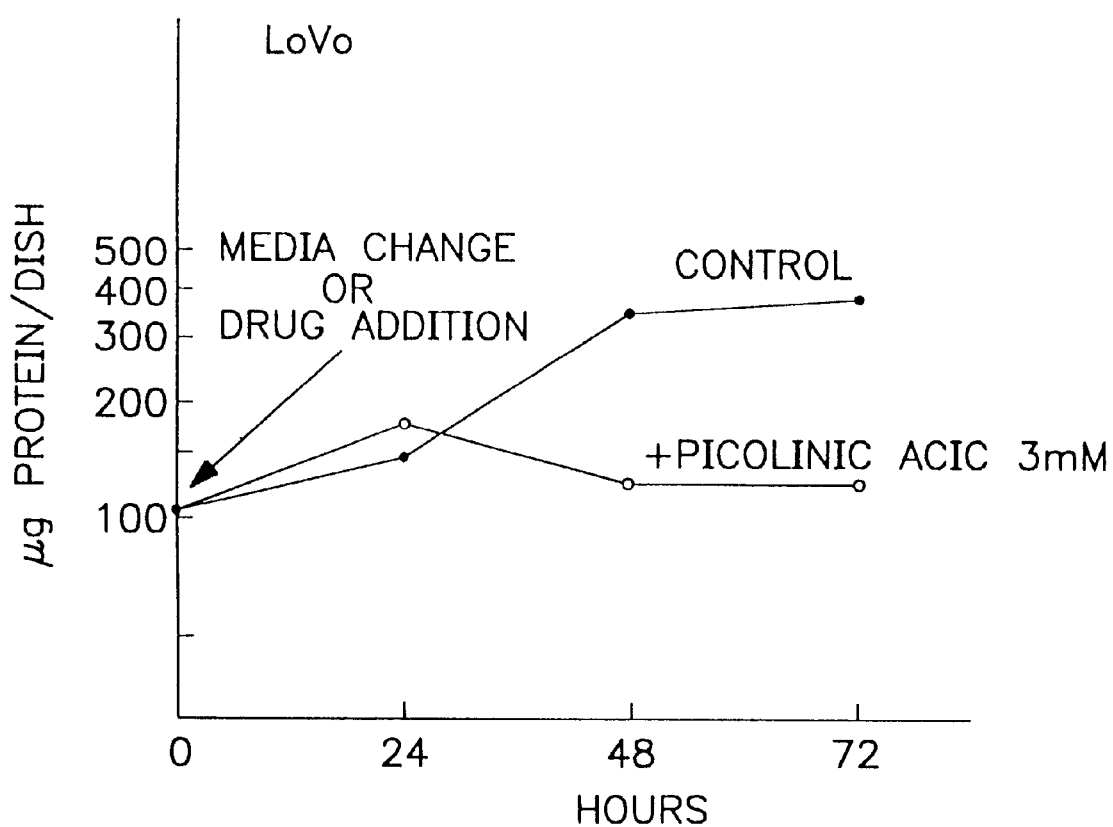
FIG. 2 illustrates the effect of picolinic acid on total protein of LoVo cells.

The growth of LoVo cells was inhibited by 3 mM picolinic acid (FIG. 2). After 24 to 48 hours of exposure to picolinic acid (3 mM), LoVo cells acquired a flattened morphology, they began to look granular, no mitosis were observed, and some began to float in the medium, (data not shown). With longer exposure (48–72 hours) cytotoxicity and cell death was observed in LoVo cells (data not shown). Equivalent results were obtained with cancerous KB cells treated with picolinic acid (3 mM) but its cytotoxic effects on this cell type were not as pronounced as in the case of LoVo cells (data not shown).

EXAMPLE 2

Effect of Fusaric Acid on Growth and Viability of Normal WI-38 cells.

In initial experiments to examine the effects of fusaric acid on cell growth and viability, WI-38 and LoVo cells were incubated for 24 to 72 hours in medium with or without various doses of fusaric acid (0.1–1 mM). The growth of both WI-38 and LoVo cells was inhibited by 500 μM fusaric acid in a time and dose dependent manner, as shown below in Table 2. A higher dose of fusaric acid (1 mM), caused a pronounced decrease in the rate of cell growth of both cell lines, and extensive cytotoxicity was noted particularly in LoVo cells by 24 hours. These preliminary experiments led to detailed tests of the effects of the highest dose of fusaric acid (500 μM) which appeared to show some differential toxicity on LoVo cells with little toxicity to WI-38 cells (Table 2).

TABLE 2

Effect of Different Doses of Fusaric Acid on WI-38 and LoVo Total Cell Protein

| | Monolayer Protein (μg/dish)[a] | | | |
|---|---|---|---|---|
| Addition | 0 h | 24 h | 48 h | 72 h |
| WI-38 | | | | |
| None | 105 | 202 | 270 | 371 |
| Fusaric acid (0.5 mM) | — | 195 | 275 | 345 |
| Fusaric acid (1 mM) | — | 236 | 202 | 195 |
| LoVo | | | | |
| None | 202 | 270 | 352 | 457 |
| Fusaric acid (0.5 mM) | — | 135 | 90 | 101 |
| Fusaric acid (1 mM) | — | ND | ND | ND |

[a]Cells were plated at $1.5 \times 10^5$ cells/60-mm dish in DME/F12 medium containing 10% Calf serum. The medium was removed 24 hours later and then fresh media containing the indicated concentrations of fusaric acid were added. Protein was determine at the indicated times. Points are the mean of duplicate determinations. SE did not exceed 5% of the mean. ND, not done because of extensive cell destruction.

Figure 3A:
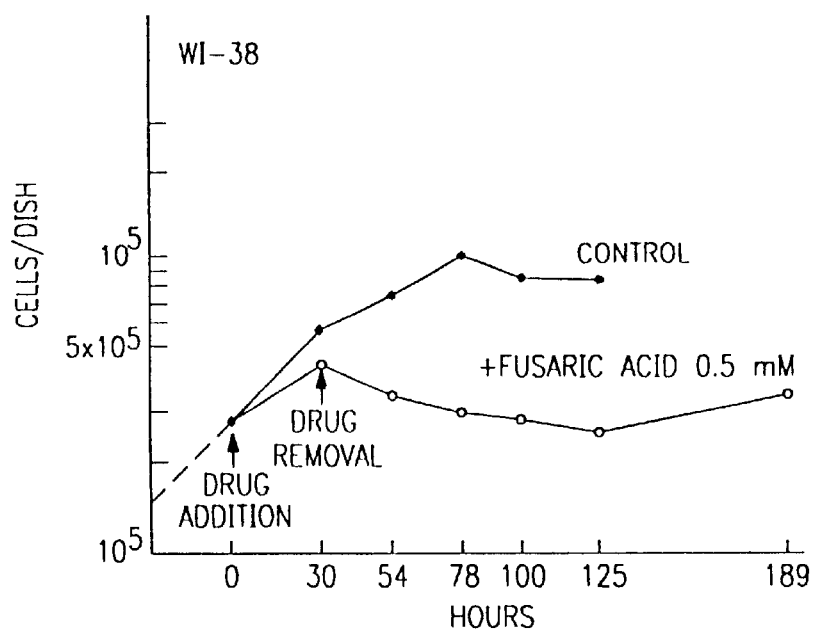
FIG. 3A illustrates the effects of fusaric acid on the growth of WI-38 cells.
Figure 3B:
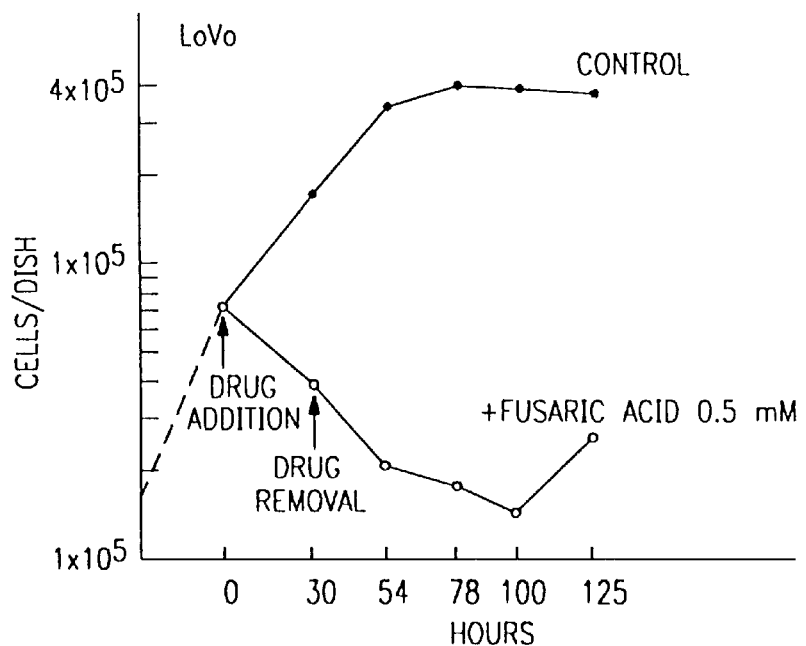
FIG. 3B illustrates the effects of fusaric acid on the growth LoVo cells.

FIG. 3A shows that the growth of WI-38 cells was strongly inhibited by 500 μM fusaric acid. After 30 to 48 hours in 500 μM fusaric acid, WI-38 cells acquired a more flattened morphology, showed some granularity, and no mitotic cells, as illustrated in FIG. 3B, or further increase in cell number were observed (See, FIG. 3A). Following 30 hours incubation with fusaric acid (500 μM), normal growth rate was not restored after removal of fusaric acid and the cell number decreased significantly (30%) after 4 days in normal media. The remaining cells were spread on the substratum in normal manner without any visible mitosis for 4 days after removal of the drug. However, they resumed growth after 125 hours of removal of fusaric acid (FIG. 3A), and most (>95%) of the cells survived. These results suggest that the majority of WI-38 cells were arrested in $G_1(G_0)$ by fusaric acid and they proceeded slowly through the cell cycle after its removal.

To examine WI-38 cell viability in greater detail, the effects of fusaric acid were studied in logarithmically growing and contact inhibited confluent cells (Tables 2 and 3). In logarithmically growing WI-38 cells approximately 76% of the cells were viable after 30 hours of treatment with fusaric acid. When the cells were treated for 78 hours, only 26% of the cell population survived the pronounced cytotoxic actions of fusaric acid The data are shown below in Table 3.

TABLE 3

Viability of Cells in Logarithmic Growth After Treatment with Fusaric Acid[a]

| Cell line | % Survival[b] | |
| --- | --- | --- |
| | 30 h | 78 h |
| WI-38 | | |
| Control | 100 | 100 |
| Treated | 76.4 | 26 |
| LoVo | | |
| Control | 100 | 100 |
| Treated | 38.5 | 4.5 |

[a]The cells were incubated in medium with or without 500 μM fusaric acid for the indicated times.
[b]Fraction of total cells counted which did not stain with trypan blue. Cells attached to the dish were exposed to trypan blue and counted. The percentage exclusion by untreated cultures was normalized to 100% for comparison with fusaric acid-treated cultures.

The detach cells showed conspicuous cytotoxic effects and most of them were destroyed. Interestingly, in confluent cell, fusaric acid did not show any cytotoxic effects as determined by the fact that 100% of the cells survived 48 hours of treatment with 500 μM fusaric acid, as shown in Table 4, below.

TABLE 4

Viability of Confluent Cells after Treatment with Fusaric Acid (500 μM)

| Cell line | % Survival[a] | |
| --- | --- | --- |
| | Control | Treated |
| WI-38 | 100 | 100 |
| LoVo | 100 | 40 |
| KB | 100 | 95 |

[a]Determined at 48 h using trypan blue dye exclusion test as indicated in Table 3.

Thus, a significant proportion of the population of growing cells (76%) and all of the confluent WI-38 cells cell resisted the marked cytotoxic action of fusaric acid.

EXAMPLE 3

Effect of Fusaric Acid on Growth and Viability of Colon Carcinoma LoVo Cells.

Fusaric acid (500 μM) inhibited LoVo cell growth, as shown in FIG. 3B. After 30 hours of treatment with 500 μM fusaric acid, there was a prominent decrease in cell number. DNA synthesis was completely (100%) inhibited by 24 hours. When treated with 500 μM fusaric acid, the majority of the LoVo cells acquired a rounded morphology by 48 hours.

As shown in FIG. 4D, most of the cells became granular, showed pronounced cytotoxic effects, many were destroyed, and subsequently detached from the culture dish. These floating cells were not viable. They did not adhere to the substratum and disintegrated after 1 to 3 days when resuspended in fresh medium without fusaric acid. FIG. 4B shows that within 30 hours of treatment there was a 60% decrease in cell number. Following removal of the drug after 30 hours of treatment showed that the cell population continued to decline (~80%) in number up to approximately 100 hours (FIG. 4B). However, after 100 hours, an increase in cell number was noted after 25 additional hours.

As in the case of Wl-38, LoVo cell viability after fusaric acid treatment was investigated in logarithmically growing and confluent cells, as shown in Tables 2 and 3. In logarithmically growing LoVo cells, approximately 38% of the attached cells were viable after 30 hours of treatment with fusaric acid. When the cells were treated for 78 hours, only 4.5% of the cell population survived the pronounced cytotoxic actions of fusaric acid. The detach cells showed noticeable cytotoxic and most of them were destroyed at these time points. In confluent cell, fusaric acid showed a significant cytotoxic effect as determined by the fact that only 40% of the cells survived 48 hours of treatment with 500 μM fusaric acid. Thus, LoVo cells are much more sensitive to the cytotoxic actions of fusaric acid in both growing and confluent population of cells in comparison to normal Wl-38 cells.

EXAMPLE 4

Effect of Fusaric Acid on Growth and Viability of Human Carcinoma KB Cells.

Figure 3C:
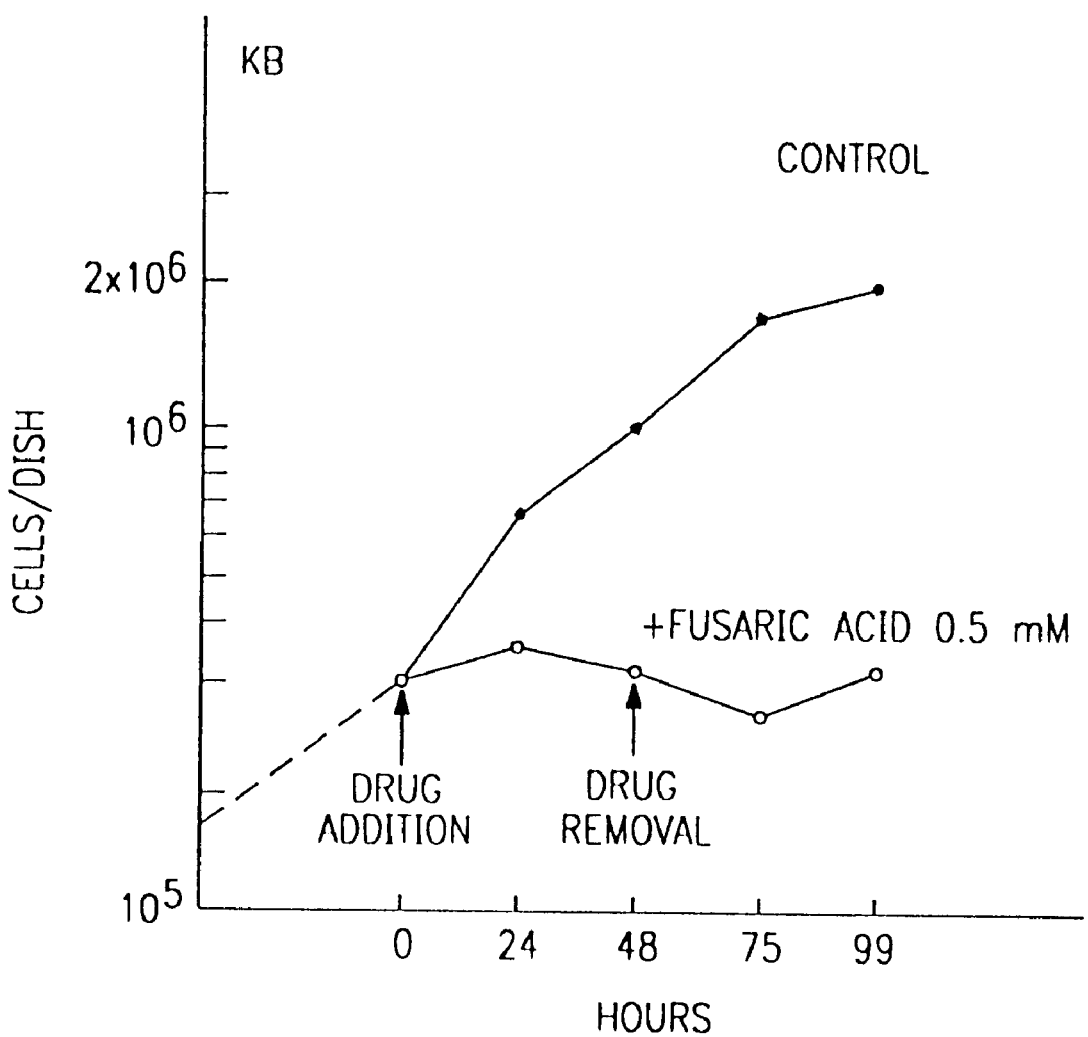
FIG. 3C illustrates the effects of fusaric acid on the growth of KB cells.

FIG. 2C shows that the growth of KB cells was inhibited by fusaric acid (500 μM). After 24 hours of treatment there was no further increase in cell number. As illustrated in FIGS. 3C and 5B, after 24–48 hours in 500 μM fusaric acid, most of the KB cells acquired a more flattened morphology, and no mitotic cells or further increase in cell number were observed. Following 48 hours incubation with fusaric acid (500 μM), normal growth rate was not restored after removal of fusaric acid and the cell number decreased significantly after 27 additional hours in normal media (FIG. 3C). The remaining cells were spread on the substratum in normal manner without any visible mitosis for 27 additional hours after drug removal. However, they resumed growth after 27 hours of removal of fusaric acid (FIG. 3C).

To examine KB cell viability in greater detail, the effects of fusaric acid were studied in logarithmically growing and confluent cells. In logarithmically growing KB cells 70% of the cells were viable after 48 hours in 500 μM fusaric acid. In confluent cell, fusaric acid did not show significant cytotoxic effect, as determined by the fact that 95% of the cells survived 48 hours of treatment with 500 μM fusaric acid (See Table 4, above). Thus, in contrast to LoVo cells, a significant proportion of the population of growing (70%) cells and virtually all (95%) of confluent KB cells resisted the pronounced cytotoxic action of fusaric acid (See Tables 3 and 4, above).

EXAMPLE 5

Effect of Fusaric Acid on Growth and Viability of Human Breast Adenocarcinoma Cells.

Fusaric acid (500μM) rapidly inhibited human breast adenocarcinoma MDA-468 cell growth. After 12–24 hours of treatment with 500 μM fusaric acid, there was no further increase in cell number. DNA synthesis was completely inhibited (100%) by 24 hr. When treated with 500 μM fusaric acid, the majority of the MDA-468 cells became granular, showed pronounced cytotoxic effects, many were destroyed and subsequently detached from the culture dish. These floating cells were not viable. Within 30 hours of treatment there was a 65% decrease in cell number. Following removal of the drug after 30 hours of treatment showed that the cell population continued to decline in number. After 96 hours, less than 10% of the original population remained attached to the dish and no change in cell number was noted after one additional week.

As in the case of WI-38, MDA-468 cell viability after fusaric acid treatment was investigated in logarithmically growing and confluent cells. In logarithmically growing MDA-468 cells, less than 20% of the attached cells were viable after 30 hours of treatment with fusaric acid. When the cells were treated for 48 hours, only 0.1% of the cell population survived the pronounced cytotoxic actions of fusaric acid. In confluent cells, fusaric acid showed significant cytotoxic effect as determined by the fact that only 10% of the cells survived 48 hours of treatment with 500 μM fusaric acid. Thus, MDA-468 cells are extremely sensitive to the cytotoxic actions of fusaric acid in both growing and confluent population of cells in comparison to normal WI-38 lines studied.

Thus, fusaric acid is effective to reduce and control growth of this common type of human malignancy.

EXAMPLE 6

Effects of fusaric acid on growth and viability of other human carcinoma cell types As in previous examples, the following human cell lines were inhibited by similar concentrations of fusaric acid: Prostatic adenocarcinoma, skin carcinoma, colon carcinoma, liver adenocarcinoma and lung adenocarcinoma. For all these cell types, cell viability decreased by approximately 60% after 48 hours of treatment with fusaric acid.

EXAMPLE 7

Combined effects of fusaric acid and standard chemotherapeutic agents.

Other chemotherapeutic agents such as 5-fluorouracil and/or levamisole in the case of colon adenocarcinoma may be utilized in conjunction with fusaric acid to enhance the effectiveness of therapy. Irreversible cell death and biological alterations induced by fusaric acid also may be enhanced by using agents from the group consisting of anti-cancer antibodies, radioactive isotopes, and chemotherapeutic agents.

The method of using fusaric acid or picolinic acid topically to treat a variety of viral and spontaneous proliferative diseases in human and animal subjects, as will be described in detail below, can be used in combination with cytotoxic agents selected from the group consisting of chemotherapuetic agents, antibodies, radioactive isotopes, and cytokines (e.g. Interferons), vitamin A, for enhanced activity.

EXAMPLE 8

Fusaric Acid effect on cells with increased P-protein activity.

Multidrug resistance (MDR) is a formidable obstacle to effective cancer chemotherapy. Studies have indicated that MDR is a phenomenon in which resistance to one drug is associated with resistance to a variety of unrelated drugs. Thus, even when a combination of chemotherapeutics is used, patients may exhibit concurrent resistance to some or all of the drugs, leading ultimately to failure of therapy.

One of the primary contributors to MDR is a glycoprotein denoted P-glycoprotein of molecular weight 170 Kdal, also know as P170. P-glycoprotein or P170 acts as a pump, effectively eliminating chemotherapeutic agents from the cell interior to the extracellular space. Although drug-sensitive cells are destroyed during the initial and subsequent courses of chemotherapy, drug resistance cells, containing elevated levels of P-glycoprotein, emerge, multiply and eventually lead to death of the host.

P-glycoprotein, the product of the mdr-1 gene is a plasma membrane protein. The molecule is composed of 12 transmembrane domains and two binding sites for ATP, which furnishes the energy required for drug elimination. The function of this protein in normal cells is presumably to eliminate naturally occurring toxic compounds. Elevated levels of P-glycoprotein have been associated with multidrug resistance in numerous malignancies, including: colon carcinoma, breast carcinoma, liver, pancreas, lung carcinoma and other tumors.

From the previous information, it is evident that drugs that are not neutralized by the P-glycoprotein mechanism will be of benefit for chemotherapeutic attack of susceptible and MDR-resistant cells. Of considerably interest for this invention is the data showing that fusaric acid does not induce P170 protein and is effective in controlling growth of cells with high levels of P170 protein. Thus, fusaric acid may have some role in the treatment of tumors which are resistant to MDR-associated drugs.

EXAMPLE 9

Use of fusaric acid to reduce the expression of retroviral mRNA levels

By using Kirsten (K) sarcoma retrovirus-transformed NRK cells it was shown in preliminary experiments that fusaric acid reduces the expression of retroviral mRNA levels. Furthermore, it also may be shown that the combination of fusaric acid and interferon-gamma results in a potent inhibition of K sarcoma virus mRNA expression in K-NRK cells.

Identification of fusaric acid as a substance that can inhibit expression of mRNA controlled by a retroviral promoter is a great interest because of the importance of retroviruses, such as the human immunodeficiency virus (HIV), in animal and human disease. Although the biology of K-virus and HIV is different, fusaric acid may be effective in controlling HIV viral expression. Furthermore, the combination of fusaric acid plus interferon-gamma may be much more potent in inhibiting HIV expression in human monocytes and other infected cells. Thus, this inventions is not limited to the effects of fusaric acid in K-NRK, cells but is extended to the actions of this agent in other retrovirally infected human and animal cells.

EXAMPLE 10

Treatment of ulcerative lesion with topical picolinic acid

A subject horse had a 3 inch diameter ulcerative lesion on the left side of its neck. The lesion had a papillomatous appearance with bleeding at the tips of the papillae. The lesion was progressive, with total loss of hair over the area. The diagnosis was viral disease, i.e. papilloma virus, complicated by fungal infection. The horse was treated with conventional local antibiotic and chemical therapies for about four months. However, the agents used did not modify the course of the disease.

An aqueous solution of 10% picolinic acid in deionized water was applied every other day with a cotton swab over and around the lesion. The treatment continued for 45 days. The course of the regression of the viral lesion was a follows:

1) after 10 days of treatment, the bleeding papillae suffered central necrosis and the borders of the ulcer acquired the aspect of granulomatous proliferating healing tissue;
2) after 20 days of treatment, the healing lesion began to show hair growth in multiple areas; the diameter of the lesion was reduced to approximately 2 inches and appeared flat and clean of debris;
3) after 30 days of treatment, the lesion was about 1 inch in diameter with abundant hair growth on the borders and on the surface of the lesion;
4) at 45 days the lesion resolved with some scar tissue; hair covered all of the area; and
5) after three additional months the horse was observed without evidence of recurring disease.

EXAMPLE 11

Treatment of patients with papilloma virus skin lesions

Picolinic acid and its analogues act by chelating metal ions. In the case of the inhibition of viral replication by picolinic acid, the ion involved is zinc, which is essential to maintain the active structure of zinc finger proteins such as E6 and E7 proteins of the human papilloma viruses essential for viral replication.

Five patients ranging in age from 11 years to 52 years and each having at least one common wart induced by human papilloma viruses was treated with a topical preparation of picolinic acid. The topical preparation was either solution of 10% to 20% picolinic acid in deionized water or a topical ointment wherein 10% picolinic acid is incorporated into Aquaphor, i.e.1 g of picolinic acid in 10 g of Aquaphor. After seven days of application of the solution or ointment, central necrosis of the wart occurred. After approximately 4 to 6 weeks the warts were gone. It should be noted that there was no significant difference observed in the course of disease between the 10% and 20% solutions. However, faster resolution was seen with the ointment and is believed to be due to the continual contact time imparted by the ointment base.

EXAMPLE 12

Treatment of virus-induced plantar ulcer

A 50 year old patient with recurrent plantar wart of about 2 cm in diameter was treated with topical picolinic acid. The patient, a pathologist who had difficulty walking because of the pain caused by the ulcer, had experimented with numerous medications for more than three months without any significant results prior to treatment with the picolinic acid. It is relevant to note that many plantar ulcers are transformed into malignant tumors.

The patient was treated with a solution of 10% picolinic acid in deionized water for one week. Central necrosis was noted. He then was treated with 10% picolinic acid in Aquaphor. The ointment was placed on the ulcer and on a patch. The patch was replaced every 24 hours. After an additional three weeks the plantar ulcer resolved.

EXAMPLE 13

Treatment of metastatic disease to the skull from breast cancer

A 73 year old female with metastatic breast cancer to the skin and bone of the skull was treated with a topical preparation of 10% picolinic acid in Aquaphor. The preparation was applied to the cancerous lesions and to a bandage and changed twice daily. The multiple cancer lesions were approximately 1 to 1.5 cm in diameter. The lesions resolved with scar tissue forming after approximately 35 days.

EXAMPLE 14

Treatment of proliferative skin disorders

Several patients suffering from proliferative skin disorders such psoriasis have been included in a recent ongoing study of the anti-proliferative effects of topical picolinic acid. Preliminary information indicates that the picolinic acid has a significant effect in inducing regression of the psoriasis. The patients may be treated with a topical application of approximately 5% to 20% picolinic acid, or a derivative thereof, in an absorption base. Alternatively, the patient may be treated with a solution containing approximately 5% to 20% picolinic acid, or derivative, in deionized water. The topical preparation may be applied twice a day or in an alternative pharmacologically acceptable regimen.

EXAMPLE 15

Treatment of Actinic lesions

Two patients with actinic lesions (average of 5 lesions per patient, each lesion being approximately 3 mm to 5 mm in diameter) were diagnosed as requiring liquid nitrogen removal of the lesions. The patients received a daily application of 10% picolinic acid in Aquaphor. After approximately three weeks of treatment, the lesions were completely cured (eliminated) without any effects on normal skin.

EXAMPLE 16

Treatment of Herpes

The subject was a 58 year old Caucasian male with at least one "cold sore" or common "fever blister". The lesions was a typical herpes simplex lesion. The subject has a history of such lesions and has treated them with lip balm or Blistex® with only limited symptomatic relief. The subject applied the subject topical antiviral as a 10% aqueous solution. Within twelve hours of the first application, the subject's lesion began to shrink with a decrease in soreness and pain. After approximately 24 hours from the initial application, the lesion as almost completely healed. He made a third application approximately 36 hours after the first application. Between 36 hours and 48 hours after the initial application, the subject described the fever blister as "gone" and "healed".

EXAMPLE 17

Treatment of Herpes

The subject was a Caucasian female in her mid-fifties with a long history of recurring, painful herpes simplex lesions described as "fever blisters". The subject presented with a painful lesion on her lip. She applied a 10% aqueous solution of the subject antiviral to the lesion approximately three or four times at 12 hour intervals. She reported that the lesion was nearly gone after the third application, but made the fourth application to "make sure".

EXAMPLE 18

Treatment of Herpes

The same female subject of Example 19 reported that should could feel the characteristic "tingling" sensation in her lip that usually preceded the eruption of a "fever blister". Upon feeling the "tingling", the subject made one application of a 10% solution of the subject topical antiviral. Within 12 hours, the tingling sensation ceased and there was no eruption of a blister.

EXAMPLE 19

Treatment of Herpes

A 47 year old Caucasian female with a history of frequent herpes simplex eruptions she characterized as "cold sores" or "fever blisters". The subject presented with a rather large, painful blister on her upper lip. The subject applied a 10% aqueous solution of the subject antiviral. Within 12 hours there was a decrease in pain and soreness and she began to experience a drying of the lesion she described as "a sort of scabbing". She made a second application approximately 12 hours later. The lesions continued to resolve. At approximately 36 to 48 hour after the initial application the lesion was described as "pretty well gone".

EXAMPLE 20

Treatment of Herpes

The subject was a 17 year old Caucasian male who presented with numerous painful white sores in his mouth and throat areas typically described as "stomach sores" or herpes. The subject suffered from the lesions for approximately two days. He could barely eat solid food due to the discomfort and pain. Before bedtime on day two, the subject took approximately ½ ounce of a 10% aqueous solution of the subject antiviral and swished it around in his mouth and spit it out. Upon awakening, approximately 8 hours later, the subject reported his mouth did not hurt, but that the sores were still there. He applied a second dose in a similar manner that morning. That evening he reported that he could eat without pain, but felt that one or two "spots" were still tender. He made no more applications. At approximately 24 hours from the first application, the subject reported that his mouth was healed.

EXAMPLE 21

Treatment of Chickenpox

The subject was a 10 year old female Caucasian presenting with typical chickenpox. The subject developed the typical rash on her torso, particularly her back and abdomen. When the rash was still in its early stages, before full-blown blistering occurred, groups of the lesions were marked by encircling with an indelible marker. A 10% solution of the subject antiviral was applied to the lesions inside the marked areas. These lesions did not erupt into blisters and the subject reported that the treated areas did not itch like the others.

PREPARATIONS CONTAINING METAL CHELATING PICOLINIC ACID AND DERIVATIVES FOR THE TREATMENT AND PREVENTION OF SPECIFIC DISEASE STATES

EXAMPLE 1

Topical or intravaginal preparation of picolinic acid in a absorption base

A topical or intravaginal preparation of picolinic acid in an absorption base is made by incorporating 0.001% to 99.9%, preferably 1% to 50%, most preferably 5% to 20% picolinic acid into an absorption base. An absorption base generally is an anhydrous base which has the property of absorbing several times its weight of water to form an emulsion and still retain an ointment-like consistency. Absorption bases may vary in their composition but generally are a mixture of animal sterols with petrolatum, such as Hydrophilic Petrolatum, U.S.P. The most common commercially available products are Eucerin and Aquaphor (Beiersdorf) and Polysorb (Fougera). One preferred embodiment of the topical preparation is made by dissolving 10% picolinic acid in deionized water and then incorporating the solution into an equal amount of Aquaphor, on a wt/wt basis. Further, the picolinic acid or derivatives can be incorporated into a balm or stick for application to the lips to treat herpes infections. It will be appreciated that picolinic acid derivatives can be used in place of the picolinic acid in the topical preparation. It will be appreciated that an appropriate concentration of a substituted picolinic acid derivative can be used in place of the picolinic acid without departing from the scope of the invention. It will be appreciated that such preparations can be used to treat topical conditions such as virus infections, fungal infections, susceptible bacterial infections, radiation assault, including ultraviolet, medical or atomic radiation, skin cancers or any other condition mediation by the above described mechanisms.

EXAMPLE 2

Picolinic acid solution

Picolinic acid can be employed topically, for vaginal installation, for inhalation or as a mouthwash as a 0.001% to 99.9%, preferably 1% to 50%, most preferably 5% to 20% aqueous solution. One preferred embodiment of the solution is prepared by dissolving an appropriate amount of picolinic acid in an appropriate amount of deionized water to form a 10% solution. The preparation can be used in any pharmaceutically acceptable manner including topically, orally, on the mucosa and so forth. It will be noted that picolinic acid derivatives can be used in place of the picolinic acid, if desired. For inhalation purposes, the solution may be atomized with the use of an appropriate device.

As stated above, it is likely that picolinic acid will interfere with the replication of the retroviruses by chelating zinc and preventing the activity of certain zinc finger proteins. Therefore, a suitable preparation of a chelating material, for example, picolinic acid or derivative may be used for vaginal application to prevent infection with any virus containing zinc finger proteins as an essential component of the viral replicating machinery, i.e. transcription factors. Such viruses include, but are not limited to, human papilloma viruses (E6 and E7 zinc finger proteins) and the AIDS virus (tat protein). As explained above, the picolinic acid and substituted derivatives thereof are used to attack the p7 protein having two zinc finger segments which is found in the HIV virus which causes AIDS, which is essential for packaging RNA in the viral particles.

The preparation may be prepared by incorporating approximately 5% to 20% picolinic acid in a suitable base, such as Aquaphor, and instilling the ointment vaginally before coitus. It also may be possible to prepare a douche of approximately 0.001% to 99.9%, preferably 1% to 50%, most preferably 5% to 20% picolinic acid in deionized water and used before and after coitus. Such preparations may be used prophylactically to prevent infection with these viruses.

Furthermore, the preparations may be used vaginally to treat the uterine cervix infected with papilloma virus.

A condom containing approximately 5% to 20% picolinic acid or derivative may be used to prevent replication of the viruses in the vaginal and cervical cells in the event the condom fails or ruptures. It will be appreciated that an appropriate concentration of a substituted picolinic acid derivative can be used in place of the picolinic acid without departing from the scope of the invention.

EXAMPLE 3

Ocular Preparation

A preparation of picolinic acid or a derivative thereof can be prepared for the treatment of ocular herpes or other retroviral infections of the eyes. The topical or intraocular ophthalmological preparation includes approximately 0.01% to approximately 5% picolinic acid or one of its substituted derivatives in an appropriate, ion-free vehicle, such as methylcellulose. The preferred embodiment would include 0.01% of picolinic acid or derivative for topical ophthalmological application. However, the invention is intended to include a broader range of concentrations of picolinic acid or derivative thereof. It will be appreciated that an appropriate concentration of a substituted picolinic acid derivative can be used in place of the picolinic acid without departing from the scope of the invention.

HEAT SHOCK PROTEINS, VIRAL INFECTION AND INFLAMMATORY RESPONSE

Prokaryotes and eukaryotes express numerous heat shock proteins (Hsps) in response to stress, including heat shock, exposure to heavy metals, hormones and viral infections. These heat shock proteins mediate and exacerbate the inflammatory response. Furthermore, Hsp27, the most common hsp found in mammals and has been shown to be involved in cancer, such as breast cancer. An increase in cellular levels of Hsp27 and Hsp70 increase the resistance of cancer cells to apotosis.

The stress response which includes numerous forms or physiological and pathological stresses is involved in viral infection also. A prominent feature of this response is the synthesis of a discrete set of proteins, know as the heat shock proteins which, at present, are denoted molecular chaperons. The role of these proteins are illustrated schematically in FIG. 13. During infection by certain viruses, heat shock proteins act as intracellular detectors that recognize malfolded proteins. In general aberrant protein folding and degradation reactions caused by exogenous or endogenous factors have emerged as a cause of cancer and aging. Researchers have found that viruses are able to activate heat shock proteins. For example, Hsp70 (DnaK) is induced by adenovirus, herpes virus, cytomegalovirus, and other viruses. DnaJ proteins are zinc finger proteins, defined by the J domain, which is essential for stimulation of the Hsp70 (DnaK) ATPase activity. Thus, the results suggest that there may be a relationship between the stress response and the cytopathic effects of certain viruses such as herpes viruses. Hsp70 has a protective role in inflammation, infection and a regulatory role in cytokine biosynthesis. Hsp70 exists in cells in equilibrium between its free state, in the cytoplasm, and its bound state, protecting proteins in the nucleolus, interacting with ribosomal proteins to either refold some of the unfolded ribosomal proteins or by solublizing the denatured ribosomal proteins to facilitate their use and increase turnover rate. During release from heat shock and as the nucleolus begins to recover its normal activities, a significant portion of Hsp70 returns to the cytoplasm. The inventor believes this protein-protein interaction has profound implications for viral replication, since viruses control ribosomal protein synthesis and during such process many of them damage the cells. Hence cellular inflammatory responses to viral infection are part of the organism defense against viruses. The compounds and methods of the present invention can be used to block the action of the DnaJ zinc finger proteins when excessively expressed. By blocking the DnaJ zinc finger proteins, which are essential for stimulation of the Hsp70 (DnaK) ATPase activity, the Hsp70 destroying activity of Hsp70 ATPase enzyme will be inhibited, thus blocking the effect of the Hsp70. This blocking of the DnaJ zinc finger protein which is required for the enzyme activity, therefore, will reduce the stress reaction in virally infected cells.

Furthermore, it is believed that the response of cells to stress, such as exposure to UV radiation, chemicals, bacteria, parasites or fungi is associated with the induction of heat shock proteins. The inventor has successfully used formulations of 1%, 5% or 10% picolinic acid in an appropriate vehicle, such as an absorption base, to treat sunburn in over 25 cases. Hence, the compounds and methods of the present invention can be used to block inappropriate and excessive cellular stress response caused, in this example, by UV radiation. Moreover, the inventor has successfully treated the inflammation associated with acne in more than 35 cases, in both adults and teenagers, with a 5% to 10% aqueous solution of picolinic acid. As determined by computer modeling, the compound binds with DnaJ and reduces or eliminates the effect of the DnaJ blocking zinc finger proteins inactivating enzymes and hence controls the inflammatory response induced by bacteria in common acne.

Presently recognized disease states involving inflammatory responses that may be susceptible to the inventor's methods also include arthritis, Alzheimer's disease. Furthermore, Arterosclerosis has an inflammatory and proliferative component which may be blocked by the instant compositions and methods. By way of further example, it is known that inflammatory cytokines play some role in Alzheimer's disease. Inflammatory molecules and mechanisms are present in the disease and inflammation may be an essential component of the disease sufficient to cause neurodegeneration. Thus, suitable doses of the disclosed picolinic acid derivatives, particularly those shown to cross the blood-brain barrier, can be used to treat the inflammatory component of the disease. Furthermore, the claimed invention is intended to apply to other pathological conditions which involved inflammatory responses both presently known and unknown.

It will be appreciated by those skilled in the art that the inventor has disclosed the best mode by which he presently understands picolinic acid and its derivatives, to function in controlling inflammatory response. However, the scope of the appended claims is intended to include other mechanisms of action, both presently known and unknown, which include metal ion containing proteins as mediators in the inflammatory response including, but not limited to, parasitic diseases such as toxoplasmosis and malaria.

VIRUS AND CANCER VACCINE

It is clearly established that zinc finger proteins of viruses are essential for viral replication and that mutations of the zinc finger domain produce non-infective viral particles. Thus, the zinc finger domain is an essential component of the virus, without which it cannot replicate, exit from the cells and infect other cells. Moreover, since the zinc finger domain is highly conserved, it generally does not mutate. However, when and if the zinc finger domain does mutate, the mutation is lethal, that is, the virus dies.

Based upon the foregoing understanding of the function and activity of metal ion containing proteins (metalloproteins), the inventor has discovered a method of preparing vaccines using metalloproteins essential for virus replication and packaging of viruses. In general, a virus is treated with the metal chelating agent, picolinic acid or one of the afore described derivatives or other suitable derivatives, for example, which denatures the zinc finger proteins of the virus. The picolinic acid, for example, distorts the protein configuration to such an extent that it becomes immunogenic and new antigenic sites are exposed. Thus, the patient develops antibodies against viral replicases and viral proteins involved in packaging the viruses.

Generally speaking, the method includes an antigenic approach to virus and cancer treatment using zinc finger protein-antigen complexes derived from an individual patient's tumors or virus-containing tissues as well as zinc finger protein-antigen complexes derived from non-autologous tissue sources. The resulting vaccines are used to stimulate a cellular immune response against viruses, primary tumor cells as well as metastasis.

More specifically, in method of the present invention the DNA or RNA is removed by standard nucleic acid technology and discarded. After removal of the nucleic acid, the viral metalloproteins are mixed with the picolinic acid or a derivative thereof in an emulsion to prevent renaturation of proteins by binding to metal ions. The zinc finger proteins are captured by beads derivatized with an analog of picolinic acid containing a side chain at the 5 position, or other suitable position, of sufficient length to allow binding of the protein to the picolinic acid metal ion. The zinc finger proteins then are conjugated to an immunogenic protein such as keyhole limpet hemocyanin (KLH), for example as taught in U.S. Pat. No. 5,243,041 (Re. 35,583). The final antigen, consisting of the KLH-zinc finger protein-picolinic acid derivative. The picolinic acid derivative is covalently bonded to the zinc finger protein to prevent renaturization of the zinc finger protein. The proteins are injected into animals following standard schedules.

Vaccines against certain viruses, particularly against HIV are difficult to produce. The ineffective nature of the hosts natural immune response indicates that a vaccine affective against HIV must provide highly specific protective immunity and, more important, must provide sterilizing immunity. This problem is compounded by the large number of HIV-1 strains. In fact, HIV-1 can be considered a quasi-virus that mutates continuously and thus vaccines for one strain are not cross-reactive or only minimally neutralizing for different strains, even in the same patient. However, the present method of preparing a vaccine using a highly conserved zinc finger protein derived from HIV will have cross antigenicity and will overcome problems associated with known methods of vaccinating against HIV.

It will be appreciated also that metalloproteins have been shown to play an important role in cancer. Metalloproteins, such as MPS-1 have growth stimulating functions that may be implicated in cancer cell proliferation and in metastasis. Thus, a vaccine, prepared as described above with reference to viral metalloproteins can be used to immunize patients against the deleterious effects of zinc finger proteins or other metalloproteins that play a role in cancer cell growth and proliferation.

It will be appreciated that various changes and modifications may be made in the preparations and methods described and illustrated without departing from the scope of the appended claims. It will be appreciated that the description of the specific embodiments of the preparation for topical use is intended to include pharmacologically accepted concentrations of the above described substituted derivatives of picolinic acid, as well as the picolinic acid itself. Oral or injectable forms of the preparations also are contemplated by the invention. Further, suitable preparations, other than topical preparations, of metal chelating compounds may be employed for the treatment of adenocarcinomas and squamous cell carcinomas. The preparation may be used alone or in combination with other chemotherapeutic agents. The picolinic acid or derivative can be included with various chemical or mechanical carriers, both known and heretofore unknown, to allow penetration or entry into tumors. Furthermore, the preparations may be used to treat a wide spectrum of proliferative and viral diseases mediated by zinc finger proteins, zinc ring proteins or other metal ion dependent proteins or enzymes. Therefore, the foregoing specification and accompanying drawings are intended to be illustrative only and should not be view in a limiting sense.

What is claimed is:

1. A method of inactivating a virus containing a metal-protein complex comprising the step of exposing said virus to a metal chelating agent so that the metal chelating agent chelates said metal within said metal-protein complex so as to denature said protein and inactivate the virus, wherein said metal chelating agent is represented by the following structure:

$$\underset{R_4}{\overset{R_3}{\diagdown}}\underset{N}{\overset{R_2}{\bigcirc}}\underset{COOH}{\overset{R_1}{\diagup}}$$

or a pharmacologically acceptable salt thereof, wherein $R_1$, $R_2$, $R_3$ and $R_4$ are selected from the group consisting of a peptide of sixteen amino acids, carboxyl group, methyl group, ethyl group, propyl group, isopropyl group, butyl group, isobutyl group, secondary butyl group, tertiary butyl group, pentyl group, isopentyl group, neopentyl group, fluorine, chlorine, bromine, iodine, and hydrogen;

wherein said metal chelating agent is not a zinc-picolinate complex prior to exposure to said virus.

2. A method of controlling viral replication comprising contacting cells infected with a virus with a metal chelating agent to induce apoptosis in the virally infected cell by chelating a metal ion in a metal ion containing cell protein wherein said metal chelating agent is represented by the following structure:

$$\underset{R_4}{\overset{R_3}{\diagdown}}\underset{N}{\overset{R_2}{\bigcirc}}\underset{COOH}{\overset{R_1}{\diagup}}$$

or a pharmacologically acceptable salt thereof, wherein $R_1$, $R_2$, $R_3$ and $R_4$ are selected from the group consisting of a peptide of sixteen amino acids, carboxyl group, methyl group, ethyl group, propyl group, isopropyl group, butyl group, isobutyl group, secondary butyl group, tertiary butyl group, pentyl group, isopentyl group, neopentyl group, fluorine, chlorine, bromine, iodine, and hydrogen;

wherein said metal chelating agent is not a zinc-picolinate complex prior to contact with said infected cells.

3. The method of claim 1 wherein $R_3$ is a butyl group.

4. The method of claim 1 wherein said metal is zinc.

5. The method of claim 1 wherein said virus is at least one virus selected from a group of viruses consisting of papilloma viruses, herpes viruses, retroviruses, human immunodeficiency viruses, viruses that cause plantar ulcers, and hepatitis viruses.

6. The method of claim 1 wherein said step of exposing said virus to said metal chelating agent comprises administering said agent to said metal-protein complex by at least one method of administration selected from a group of methods of administration consisting of injection, oral administration, inhalation, transdermal administration, parenteral administration, rectal administration, intraperitoneal administration and intravaginal administration.

7. The method of claim 1 further comprising the step of adding said metal chelating agent to a treatment regimen of one or more chemotherapeutic agents.

8. The method of claim 5 wherein said virus is a papilloma virus and said papilloma virus is exposed to a preparation consisting of a solution of about 10% to about 20% said metal chelating agent and an ointment.

9. The method of claim 6 wherein said administration is intravaginal administration and said virus is exposed to about 5% to about 20% said metal chelating agent and an ointment.

10. The method of claim 6 wherein said metal chelating agent is administered intravaginal by a douche that includes 0.001% to about 99.9% of said metal chelating agent.

11. The method of claim 5 wherein said virus is a retroviral infection of the eye and exposing said virus to said metal chelating agent comprises the administration of approximately 0.01% to approximately 5% said metal chelating agent topically or intraocularly.

12. The method of claim 1 wherein said virus is exposed to a preparation comprising of about 5% to about 20% of said metal chelating agent and a diluent.

13. A method of inactivating a virus containing a metal-protein complex comprising the step of exposing said virus to a metal chelating agent so that the metal chelating agent chelates said metal within said metal-protein complex so as to denature the protein and inactivate the virus, said metal chelating agent represented by the following structure:

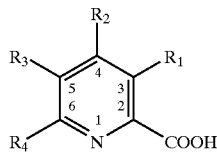

or a pharmacologically acceptable salt thereof,
wherein $R_1$, $R_2$, and $R_4$ are selected from the group consisting of a peptide of sixteen amino acids, carboxyl group, methyl group, ethyl group, propyl group, isopropyl group, butyl group, isobutyl group, secondary butyl group, tertiary butyl group, pentyl group, isopentyl group, neopentyl group, fluorine, chlorine, bromine, iodine, and hydrogen; and
$R_3$ is a butyl group.

14. The method of claim 2 wherein $R_3$ is a butyl group.

15. The method of claim 2 wherein said metal is zinc.

16. The method of claim 2 wherein said virally infected cell is at least one cell selected from a group of cells consisting of human carcinoma cells, human breast adenocarcinoma cells, prostatic adenocarcinoma cells, skin adenocarcinoma cells, colon adenocarcinoma cells, liver adenocarcinoma cells, lung adenocarcinoma cells, LoVo cells, KB cells, Kirsten sarcoma cells, and retrovirus-transformed NRK cells.

17. The method of claim 2 wherein said step of contacting said infected cells is by at least one method of administration selected from a group of methods of administration consisting of injection, oral administration, inhalation, transdermal administration, parenteral administration, rectal administration, intraperitoneal administration, and intravaginal administration.

18. The method of claim 2 wherein said virus is at least one virus selected from a group of viruses consisting of papilloma viruses, herpes viruses, a retrovirus, human immunodeficiency viruses, a virus that cause plantar ulcers and hepatitis viruses.

19. The method of claim 2 further comprising the step of adding said metal chelating agent to a treatment regimen of one or more chemotherapeutic agents.

20. The method of claim 17 wherein said metal chelating agent is administered intravaginal and said virus is contacted with a preparation comprising about 5% to about 20% said metal chelating agent and an ointment.

21. The method of claim 17 wherein said agent is administered intravaginal and said virus is exposed to a douche that includes 0.001% to about 99.9% of said metal chelating agent.

22. The method of claim 18 wherein said virus is a papilloma virus and said papilloma virus is contacted with a preparation consisting of about 10% to about 20% of said metal chelating agent and an ointment.

23. The method of claim 2 wherein said infected cells are contacted with a preparation comprising 5% to 20% of said agent and a diluent.

24. The method of claim 18 wherein said virus is a retroviral infection of the eye and contacting said cells infected with said virus comprises the administration of approximately 0.01% to approximately 5% said metal chelating agent topically or intraocularly.

25. A method of controlling viral replication comprising contacting cells infected with a virus with a metal chelating agent to induce apoptosis in the virally infected cell by chelating a transition metal ion in a transition metal ion containing cell protein wherein said metal chelating agent is represented by the following structure:

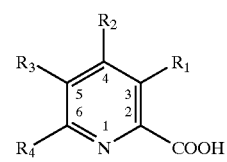

or a pharmacologically acceptable salt thereof,
wherein $R_1$, $R_2$, and $R_4$ are selected from the group consisting of a peptide of sixteen acids, carboxyl group, methyl group, ethyl group, propyl group, isopropyl group, butyl isobutyl group, secondary butyl group, tertiary butyl group, pentyl group, isopentyl group, neopentyl group, fluorine, chlorine, bromine, iodine, and hydrogen; and
$R_3$ is a butyl group.

* * * * *